US012597488B2

(12) United States Patent
Schobel et al.

(10) Patent No.: US 12,597,488 B2
(45) Date of Patent: Apr. 7, 2026

(54) USE OF MACHINE LEARNING MODELS FOR PREDICTION OF CLINICAL OUTCOMES

(71) Applicants: Henry M. Jackson Foundation for the Advancement of Military Medicine, Bethesda, MD (US); The United States of America, as Represented by the Secretary of the Navy, Silver Spring, MD (US); Duke University Medical Center, Durham, NC (US); Emory University, Atlanta, GA (US)

(72) Inventors: Seth A Schobel, Bethesda, MD (US); Vivek Khatri, Bethesda, MD (US); Felipe Lisboa, Bethesda, MD (US); Matthew J. Bradley, Silver Spring, MD (US); Christopher J. Dente, Atlanta, GA (US); Timothy Buchman, Atlanta, GA (US); Allan D. Kirk, Durham, NC (US); Jonathan A. Forsberg, Silver Spring, MD (US); Eric A. Elster, Bethesda, MD (US)

(73) Assignees: The Henry M. Jackson for the Advancement of Military Medicine, Inc., Bethesda, MD (US); The United States of America, as Represented by the Secretary of the Navy, Silver Spring, MD (US); Duke University Medical Center, Durham, NC (US); Emory Univeristy, Atlanta, GA (US)

( * ) Notice: Subject to any disclaimer, the term of this patent is extended or adjusted under 35 U.S.C. 154(b) by 714 days.

(21) Appl. No.: 17/268,882

(22) PCT Filed: Aug. 16, 2019

(86) PCT No.: PCT/US2019/046884
§ 371 (c)(1),
(2) Date: Feb. 16, 2021

(87) PCT Pub. No.: WO2020/037244
PCT Pub. Date: Feb. 20, 2020

(65) Prior Publication Data
US 2021/0327540 A1 Oct. 21, 2021

Related U.S. Application Data

(60) Provisional application No. 62/764,963, filed on Aug. 17, 2018.

(51) Int. Cl.
*G16B 40/00* (2019.01)
*G06N 20/00* (2019.01)
(Continued)

(52) U.S. Cl.
CPC ............. *G16B 40/00* (2019.02); *G06N 20/00* (2019.01); *G16B 5/20* (2019.02); *G16H 10/40* (2018.01);
(Continued)

(58) Field of Classification Search
CPC .......... G16B 40/00; G16B 5/20; G06N 20/00; G06N 3/044; G06N 3/045; G06N 5/01;
(Continued)

(56) References Cited

U.S. PATENT DOCUMENTS 11,023,824 B2 * 6/2021 Kida ....................... G06F 17/18
2014/0187519 A1 7/2014 Cooke et al.
(Continued)

FOREIGN PATENT DOCUMENTS

WO WO-2017165693 A1 * 9/2017 ............. G16H 50/20
WO WO2018204509 A1 11/2018
(Continued)

OTHER PUBLICATIONS

PCT Search Report and Written Opinion mailed on Nov. 5, 2019 for PCT Application No. PCT/US19/46884, 11 pages.

*Primary Examiner* — Eliza A Lam
(74) *Attorney, Agent, or Firm* — Lee & Hayes, P.C.

(57) ABSTRACT

The present disclosure describes methods and systems for predicting if a subject has an increased risk of having or developing one or more clinical outcomes, including prior to
(Continued)

the detection of symptoms thereof and/or prior to onset of any detectable symptoms thereof. The present disclosure also describes a method of generating a model for predicting one or more clinical outcomes.

22 Claims, 5 Drawing Sheets

(51) Int. Cl.

| | | |
|---|---|---|
| *G16B 5/20* | (2019.01) | |
| *G16H 10/40* | (2018.01) | |
| *G16H 10/60* | (2018.01) | |
| *G16H 50/20* | (2018.01) | |
| *G16H 50/30* | (2018.01) | |
| *G16H 50/70* | (2018.01) | |
| *G16H 70/20* | (2018.01) | |

(52) U.S. Cl.
CPC ............ *G16H 10/60* (2018.01); *G16H 50/20* (2018.01); *G16H 50/30* (2018.01); *G16H 50/70* (2018.01); *G16H 70/20* (2018.01)

(58) Field of Classification Search
CPC .......... G06N 7/01; G06N 3/047; G06N 20/10; G06N 20/20; G16H 10/40; G16H 10/60; G16H 50/20; G16H 50/30; G16H 50/70; G16H 70/20
See application file for complete search history.

(56) References Cited

U.S. PATENT DOCUMENTS

| | | | |
|---|---|---|---|
| 2015/0168423 A1 | 6/2015 | Gill et al. | |
| 2017/0009297 A1* | 1/2017 | Spencer ............... | C12Q 1/6883 |
| 2017/0039689 A1 | 2/2017 | Solanki et al. | |
| 2019/0355473 A1* | 11/2019 | Schobel ................ | G16H 50/30 |

FOREIGN PATENT DOCUMENTS

| | | | | |
|---|---|---|---|---|
| WO | WO2018223001 A1 | 12/2018 | | |
| WO | WO2018223006 A1 | 12/2018 | | |
| WO | WO2018223008 A1 | 12/2018 | | |
| WO | WO2018223124 A2 | 12/2018 | | |
| WO | WO-2019114081 A1 * | 6/2019 | .......... | C23C 14/042 |

* cited by examiner

Clinical Parameters
With Differential Values
400

Variable Selection
Result 402

Performance Metric
404

USE OF MACHINE LEARNING MODELS FOR PREDICTION OF CLINICAL OUTCOMES

CROSS-REFERENCE TO RELATED APPLICATION

This application is a U.S. National Phase Application of International Application No. PCT/US2019/046884 filed Aug. 16, 2019, which claims the benefit of U.S. Provisional Patent Application No. 62/764,963, filed on Aug. 17, 2018, all of which are hereby incorporated by reference in their entirety.

STATEMENT REGARDING FEDERALLY SPONSORED RESEARCH OR DEVELOPMENT

This invention was made with government support under grant USUHS HU0001-15-2-0001 and HU0001-19-2-0010 awarded by the Department of Defense and Defense Health Program. The government has certain rights in the invention.

FIELD OF THE DISCLOSURE

Described herein are systems, methods, and computational environments for predicting one or more clinical outcomes in a subject having an injury based on clinical parameters. Also described are systems and methods for predicting one or more clinical outcomes for a subject, systems and methods for generating multiple models for predicting outcomes and determining the most accurate model, and methods of treating a subject determined to have an elevated risk of a specific outcome, methods of detecting panels of biomarkers in a subject, and methods of assessing risk factors in a subject having an injury, as well as related devices and kits.

BACKGROUND OF THE DISCLOSURE

Individuals who are exposed to physical trauma (e.g. on the battlefield or major accidents) have elevated risks of injuries. The myriad potential injuries and the lack of ability to perform robust, invasive diagnostics (e.g. MRI, CT-scans, angiography) make it prohibitively difficult to accurately quantify risk of clinical outcomes and make high-fidelity decisions on treatment and intervention strategies. Having tools that would allow a clinician, either in the field or at the bedside, to predict or identify the patients at highest risk for a variety of complications could allow for more proactive and directed preventative strategies.

SUMMARY OF THE DISCLOSURE

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

Described herein are methods of determining if a subject has an increased risk of having or developing one or more clinical outcomes, including prior to the detection of symptoms thereof and/or prior to onset of any detectable symptoms thereof, methods for predicting clinical outcomes, and related methods of treatment.

The present disclosure also provides methods of treating individuals determined to have an increased risk of developing one or more of the clinical outcomes, optionally before the onset of detectable symptoms thereof, such as before there are perceivable, noticeable or measurable signs of pneumonia in the individual. Examples of treatment may include initiation or broadening of antibiotic therapy, surgery, balancing fluids and electrolytes, renal replacement therapy, adjustment of mechanical ventilation, early use of nonsteroidal anti-inflammatory drugs, hemodynamic adjustments, administration of calcium channel blocker medications, and surgical debridement. Benefits of such early treatment may include avoidance of sepsis, empyema, need for ventilation support, reduced length of stay in hospital or intensive care unit, reduced mortality, lower risk of limb loss, and/or reduced medical costs.

In embodiments, there are provided methods for predicting one or more clinical outcomes for a subject comprising, generating a training database storing first values of a plurality of clinical parameters and clinical outcomes associated with a plurality of first subjects; executing a plurality of machine learning models to select a subset of model parameters from the plurality of clinical parameters for each machine learning model; executing each one of a plurality of machine learning models for one of the plurality of subsets of model parameters to generate predictions of clinical outcomes; calculating a performance metric associated with each of the plurality of machine learning models in accordance with the predictions of clinical outcomes; selecting a candidate classification machine learning model in accordance with the performance metric; and outputting a model for predicting a clinical outcome, the model comprising the candidate classification algorithm with associated subset of model parameters.

In embodiments, there are provided methods for predicting a clinical outcome for a subject comprising, receiving, from a second subject, a second value of at least one clinical parameter of a plurality of clinical parameters; executing a pre-trained model for predicting a clinical outcome of the second subject using the second value of at least one clinical parameter, wherein the model is pre-trained by performing operations comprising, generating a training database storing first values of the plurality of clinical parameters and clinical outcomes associated with a plurality of first subjects; executing a plurality of variable selection machine learning models to select a subset of model parameters from the plurality of clinical parameters for each variable selection algorithm; executing each one of a plurality of classification machine learning models for one of the plurality of subsets of model parameters to generate predictions of the clinical outcome; calculating a performance metric associated with each of the plurality of classification algorithms in accordance with the predictions of one or more clinical outcomes; selecting a candidate classification machine learning model in accordance with the performance metric; and outputting a model for predicting the clinical outcome, the model comprising the candidate classification machine learning model with associated subset of model parameters; and outputting the predicted clinical outcome of the second subject.

In embodiments, there are provided methods for pre-processing data that is stored in the training database including, determining that a first value of at least one of the plurality of clinical parameters is missing, estimating a reference value for the at least one of the plurality of clinical parameters that is missing; and storing the reference value as the first value of the at least one of the plurality of clinical parameters in the training database.

In embodiments, the plurality of variable selection machine learning models comprise at least one of unsupervised machine learning algorithm, supervised machine learning algorithm, Backward Elimination algorithm, Grow-Shrink algorithm, Incremental Association Markov Blanket algorithm, Least Absolute Shrinkage and Selection Operator, Ridge Regression, Elastic Net, or Semi-Interleaved Hiton-PC algorithm. While these algorithms are enumerated for variable selection machine learning, many others are contemplated In embodiments, the classification algorithm comprises at least one of linear discriminant analysis, classification and regression tree, decision tree learning, random forest model, nearest neighbor, support vector machine, logistic regression, generated linear model, Bayesian model, or neural network.

In embodiments, there are provided methods for selecting a candidate classification algorithm in accordance with the performance metric further comprise executing decision curve analysis (DCA) with each classification algorithm, the DCA indicating a net benefit of providing a treatment based on clinical outcomes generated by the classification algorithm; and selecting the classification algorithm having a largest net benefit of providing the treatment as the candidate classification algorithm.

In embodiments, there are provided methods for cross-validating performances of the plurality of classification algorithms, wherein cross-validating performances comprises one or more of leave one out cross-validation, k fold, stratified cross-fold validation, time-series cross-validation.

Cross-validation is an approach to test a model's ability to predict new data that was not used in the estimation (training) of the model. Cross-validation is often used by comparing the results from one subset of a data set to another subset of the data set. For example, leave on out cross-validation is a method of cross-validation wherein one data point is removed to test the model. As another example, K-fold validation is similar to leave one out cross-validation, but the dataset is divided into k subsets, where k represents an integer; the cross-validation is repeated k times and each time one of the k subsets is used as the test set and the other k−1 subsets are put together to form a training set, then the average error across all k trials is computed. While these methods are enumerated, this list is not exhaustive and many other forms of cross-validation are contemplated In embodiments, the performance metric associated with each of the plurality of classification algorithms includes at least one of a total out-of-bag (OOB) error estimate, a positive class OOB error estimate, a negative OOB error estimate, an accuracy score, area under the curve (AUC) measure from a receiver operating characteristic (ROC) curve, sensitivity, specificity, or a Kappa score.

In embodiments, the plurality of clinical parameters comprise one or more biomarker clinical parameters, one or more administration of blood products clinical parameters, surface wound injury, abdominal injury, one or more injury severity score clinical parameters, or a combination thereof.

In embodiments, the one or more clinical outcomes may comprise: acute kidney injury, acute respiratory distress, bacteremia, heterotopic ossification, pneumonia, post-traumatic sterile inflammation, sepsis, wound closure, or vasospasm and/or mortality following traumatic brain injury (TBI). The traumatic brain injury can be a severe TBI (sTBI) or a mild TBI.

In embodiments, there are provided systems for generating a machine learning engine for predicting one or more clinical outcomes in a subject comprising: one or more processors; a memory; a communication platform; a training database configured to store first values of a plurality of clinical parameters and clinical outcomes associated with a plurality of first subjects; a machine learning engine configured to execute a plurality of variable selection machine learning models to select a subset of model parameters from the plurality of clinical parameters for each variable selection machine learning models; execute each one of a plurality of classification machine learning models for one of the plurality of subsets of model parameters to generate predictions of the one or more clinical outcomes; calculate a performance metric associated with each of the plurality of classification machine learning models in accordance with the predictions of the one or more clinical outcomes; select a candidate classification machine learning model in accordance with the performance metric; and output a machine learning model for predicting one or more clinical outcomes, the machine learning model comprising the candidate classification machine learning model with associated subset of model parameters.

In embodiments, there are provided systems for predicting one or more outcomes in a subject comprising: one or more processors; a memory; a communication platform; a training database configured to store first values of a plurality of clinical parameters and the one or more clinical outcomes associated with a plurality of first subjects; a machine learning engine configured to pre-train a model for one of more clinical outcomes outcome of a subject, wherein the model is pre-trained by performing operations comprising: generating a training database storing first values of the plurality of clinical parameters and clinical outcomes associated with a plurality of first subjects; executing a plurality of variable selection machine learning models to select a subset of model parameters from the plurality of clinical parameters for each variable selection algorithm; executing each one of a plurality of classification machine learning models for one of the plurality of subsets of model parameters to generate predictions of pneumonia outcome; calculating a performance metric associated with each of the plurality of classification machine learning models in accordance with the predictions of one or more clinical outcome; selecting a candidate classification machine learning model in accordance with the performance metric; and outputting a machine learning model for predicting the one or more clinical outcomes, the model comprising the candidate classification machine learning model with associated subset of model parameters; and a prediction engine configured to receive, from a second subject, a second value of at least one clinical parameter of a plurality of clinical parameters; and execute the pre-trained model for predicting one or more clinical outcomes of the second subject using the second value of at least one clinical parameter; and a display device configured to output the predicted one or more clinical outcomes of the second subject.

In embodiments, there is provided a non-transitory computer-readable medium having information recorded thereon for generating a model for predicting one or more clinical outcomes in a subject, wherein the information, when read by a computer, causes the computer to perform operations of: generating a training database storing first values of a plurality of clinical parameters and clinical outcomes associated with a plurality of first subjects; executing a plurality of variable selection machine learning model to select a subset of model parameters from the plurality of clinical parameters for each variable selection machine learning model; executing each one of a plurality of classification machine learning models for one of the plurality of subsets of model parameters to generate predictions of one or more clinical outcomes; calculating a performance metric associated with each of the plurality of classification machine learning models in accordance with the predictions of pneumonia outcome; selecting a candidate classification machine learning model in accordance with the performance metric; and outputting a model for predicting one or more clinical outcomes, the model comprising the candidate classification machine learning model with associated subset of model parameters.

BRIEF DESCRIPTION OF THE SEVERAL VIEWS OF THE DRAWINGS

The present disclosure can be better understood by reference to the following drawings. The drawings are merely exemplary to illustrate certain features that may be used singularly or in combination with other features and the present disclosure should not be limited to the embodiments shown.

DETAILED DESCRIPTION

Figure 1:
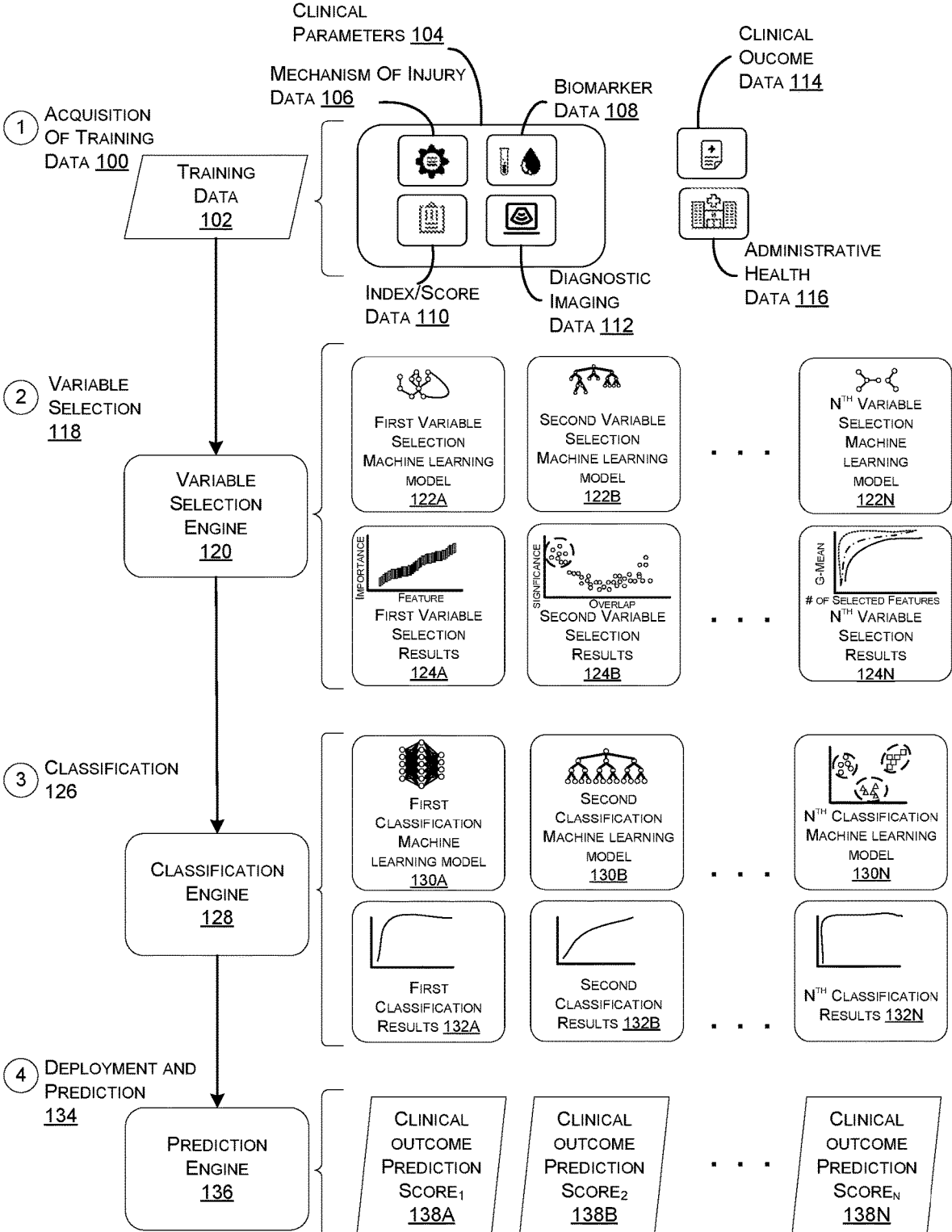
FIG. 1 depicts a method of predicting one or more clinical outcomes through a process of acquisition of training data, performing variable selection in a variable selection engine, performing classification in a classification engine, and the deploying and predicting clinical outcomes for one or more clinical outcomes.

The following detailed description is presented to enable any person skilled in the art to make and use the subject of the application. For purposes of explanation, specific nomenclature is set forth to provide a thorough understanding of the present disclosure. However, it will be apparent to one skilled in the art that these specific details are not required to practice the subject of the application. Descriptions of specific applications are provided only as representative examples. The present application is not intended to be limited to the embodiments shown but is to be accorded the widest possible scope consistent with the principles and features disclosed herein.

The present disclosure provides methods of predicting one or more clinical outcomes and adjusting treatments for individuals determined to have an increased risk of developing one or more of the clinical outcomes, optionally before the onset of detectable symptoms thereof, such as before there are perceivable, noticeable, or measurable signs of one or more clinical outcomes in the individual. The individual may be undergoing established treatment and based on the clinical outcome predicted by the methods described herein, adjustment can be made for more appropriate treatment.

Clinical outcomes include diseases or conditions that a subject can be diagnosed to have. Clinical outcomes also may involve an assessment by a health care provider or may be measurable changes in health, function, or quality of life. Clinical outcomes are obtained by the methods described herein based on clinical parameters of a subject obtained by a clinician. In embodiments, the one or more clinical outcomes includes acute kidney injury, acute respiratory distress, bacteremia, heterotopic ossification, pneumonia, post-traumatic sterile inflammation, sepsis, wound closure, or vasospasm and/or mortality following traumatic brain injury, or a combination thereof. The traumatic brain injury can be a severe TBI (sTBI) or a mild TBI.

Established acute kidney injury treatments include balancing fluids and electrolytes in addition to renal replacement therapy. Established acute respiratory distress treatments include fluid management and adjustment of mechanical ventilation to optimize tissue oxygenation and minimize hypoxia. Established bacteremia treatments include the adjustment of antibiotic treatment. Established heterotopic ossification treatments include its prevention in part by early use of nonsteroidal anti-inflammatory drugs. Established pneumonia treatments include the adjustment of antibiotic treatment. Established post-traumatic sterile inflammation with systemic inflammation treatments include a multiple assessment of biochemical, metabolic and hemodynamic profiles for individual adjustments in medication, fluid and electrolytes. Established sepsis treatment includes an immediate antibiotic treatment combined with a hemodynamic and electrolyte balance adjustments. Established TBI-induced vasospasm treatments include calcium channel blocker medications to prevent further associated complications. Established wound closure treatments include an adequate adjustment for the number of surgical debridements to allow successful healing by delayed primary closure. While these treatments for one or more clinical outcomes are discussed, many more are contemplated. Benefits of such early treatment may include avoidance of sepsis, empyema, need for ventilation support, reduced length of stay in hospital or intensive care unit, reduced mortality, lower risk of limb loss, and/or reduced medical costs.

The present disclosure also provides using the methods described herein to monitor subjects to help clinicians make decisions on adjusting treatments, when necessary.

Technical and scientific terms used herein have the meanings commonly understood by one of ordinary skill in the art to which the present disclosure pertains, unless otherwise defined.

As used herein, the singular forms "a," "an," and "the" designate both the singular and the plural, unless expressly stated to designate the singular only.

The terms "administer," "administration," or "administering" as used herein refer to (1) providing, giving, dosing and/or prescribing, such as by either a health professional or his or her authorized agent or under his direction, and (2) putting into, taking or consuming, such as by a health professional or the subject, and is not limited to any specific dosage forms or routes of administration unless otherwise stated.

The terms "treat", "treating" or "treatment", as used herein, include alleviating, abating or ameliorating pneumonia or one or more symptoms thereof, whether or not pneumonia is considered to be "cured" or "healed" and whether or not all symptoms are resolved. The terms also include reducing or preventing progression of one or more clinical outcomes or one or more symptoms thereof, impeding or preventing an underlying mechanism of one or more clinical outcomes or one or more symptoms thereof, and achieving any therapeutic and/or prophylactic benefit.

As used herein, the term "subject," "subject in need thereof," "patient," "individual," or "test subject" indicates a mammal, in particular a human or non-human primate. The test subject may or may not be in need of an assessment of a predisposition to one or more clinical outcomes. In embodiments, the test subject is assessed prior to the detection of symptoms of one or more clinical outcomes. In embodiments, the test subject is assessed prior to the onset of any detectable symptoms of one or more clinical outcomes. In embodiments, the test subject does not have detectable symptoms of any type of sickness or condition. In embodiments, the test subject has an injury, condition, or wound that puts the subject at risk of developing one or more clinical outcomes, such as having a viral or bacterial infection, such as but not limited to urinary tract infection, meningitis, pericarditis, endocarditis, osteomyelitis, and infectious arthritis, having or developing bronchitis, undergoing a medical surgical or dental procedure, having an open wound or trauma, such as but not limited to a wound received in combat, a blast injury, a crush injury, a gunshot wound, an extremity wound, suffering a nosocomial infection, having undergone medical interventions such as central line placement or intubation, having diabetes, having HIV, undergoing hemodialysis, undergoing organ transplant procedure (donor or receiver), receiving a glucocorticoid or any other immunosuppressive treatments, such as but not limited to calcineurin inhibitors, mTOR inhibitors, IMDH inhibitors and biologics or monoclonal antibodies. In embodiments, the subject does not have a condition that puts the subject at risk of developing pneumonia, prior to application of the methods described herein. In other embodiments, the subject has a condition that puts the subject at risk of developing one or more clinical outcomes.

As used herein, the term "increased risk" or "elevated risk" is used to mean that the test subject has an increased chance of developing or acquiring one or more clinical outcomes compared to a normal or reference individual or population of individuals. In embodiments, the reference individual is the test subject at an earlier time point, including prior to having an injury, condition, or wound that puts the subject at risk of developing pneumonia, or at an earlier point in time after having such an injury, condition, or wound. The increased risk may be relative or absolute and may be expressed qualitatively or quantitatively. For example, an increased risk may be expressed as simply determining the subject's risk profile and placing the subject in an "increased risk" category, based upon previous studies. Alternatively, a numerical expression of the subject's increased risk may be determined based upon the risk profile. As used herein, examples of expressions of an increased risk include but are not limited to, odds, probability, odds ratio, p-values, attributable risk, biomarker index score, relative frequency, positive predictive value, negative predictive value, and relative risk. Risk may be determined based on predicting clinical outcomes for the subject; for example, a predicted acute kidney injury outcome may include an indication of whether the subject has acute kidney injury or does not have acute kidney injury, an indication of a likelihood that the subject has acute kidney injury or does not have acute kidney injury, or an indication of a likelihood that the subject will develop acute kidney injury.

For example, the correlation between a subject's risk profile and the likelihood of suffering from acute kidney injury may be measured by an odds ratio (OR) and by the relative risk (RR). If $P(R^+)$ is the probability of developing acute kidney injury for individuals with the risk profile (R) and $P(R^-)$ is the probability of developing acute kidney injury for individuals without the risk profile, then the relative risk is the ratio of the two probabilities: $RR=P(R^+)/P(R^-)$.

In case-control studies, direct measures of the relative risk often cannot be obtained because of sampling design. The odds ratio allows for an approximation of the relative risk for low-incidence diseases and can be calculated: $OR=(F^+/(1-F^+))/(F^-/(1-F^-))$, where $F^+$ is the frequency of a risk profile in cases studies and $F^-$ is the frequency of risk profile in controls. $F^+$ and $F^-$ can be calculated using the risk profile frequencies of the study.

The attributable risk (AR) can also be used to express an increased risk. The AR describes the proportion of individuals in a population exhibiting a specific clinical outcome to a specific member of the risk profile. AR may also be important in quantifying the role of individual components (specific member) in condition etiology and in terms of the public health impact of the individual risk factor. The public health relevance of the AR measurement lies in estimating the proportion of cases of the specific clinical outcome in the population that could be prevented if the profile or individual factor were absent. AR may be determined as follows: $AR=P_E(RR-1)/(P_E(RR-1)+1)$, where AR is the risk attributable to a profile or individual factor of the profile, and $P_E$ is the frequency of exposure to a profile or individual component of the profile within the population at large. RR is the relative risk, which can be approximated with the odds ratio when the profile or individual factor of the profile under study has a relatively low incidence in the general population.

The terms "factor," "risk factor," and/or "component" are used herein to refer to individual constituents that are assessed, detected, measured, received, and/or determined prior to or during the performance of any of the methods described herein. For convenience, they are referred to herein as clinical parameters.

Clinical parameters include various factors associated with a subject experiencing symptoms of a disease or condition or in measurable changes in health, function, or quality of life. Examples of clinical parameters of a subject include, but are not limited to any one or more of level of interleukin-1α (IL-1α) in a sample from the subject, level of interleukin-Iβ (IL-Iβ) in a sample from the subject, level of interleukin-1 receptor agonist (IL-1RA) in a sample from the subject, level of interleukin-2 (IL-2) in a sample from the subject, level of interleukin-2 receptor (IL-2R) in a sample from the subject, level of interleukin-3 (IL-3) in a sample from the subject, level of interleukin-4 (IL-4) in a sample from the subject, level of interleukin-5 (IL-5) in a sample from the subject, level of interleukin-6 (IL-6) in a sample from the subject, level of interleukin-7 (IL-7) in a sample from the subject, level of interleukin-8 (IL-8) in a sample from the subject, level of interleukin-10 (IL-10) in a sample from the subject, level of interleukin-12 (IL-12) in a sample from the subject, level of interleukin-13 (IL-13) in a sample from the subject, level of interleukin-15 (IL-15) in a sample from the subject, level of interleukin-17 (IL-17) in a sample from the subject, level of tumor necrosis factor alpha (TNF-α) in a sample from the subject, level of granulocyte colony stimulating factor (G-CSF) in a sample from the subject, level of granulocyte macrophage colony stimulating factor (GM-CSF) in a sample from the subject, level of interferon alpha (IFN-α) in a sample from the subject, level of interleukin-8 (IL-8) in a sample from the subject, level of interleukin-10 (IL-10) in a sample from the subject, level of interferon gamma (IFN-γ) in a sample from the subject, level of epithelial growth factor (EGF) in a sample from the subject, level of basic fibroblast growth factor (bFGF) in a sample from the subject, level of hepatocyte growth factor (HGF) in a sample from the subject, level of vascular endothelial growth factor (VEGF) in a sample from a subject, the level of monocyte chemoattractant protein-1 (CCL2/MCP-1) in a sample from a subject, the level of macrophage inflammatory protein-1 alpha (CCL3/MIP-Iα) in a sample from a subject, the level of macrophage inflammatory protein-1 beta (CCI-4/M I P-Iβ) in a sample from a subject, the level of CCL5/RANTES in a sample from a subject, the level of CCLII/eotaxin in a sample from a subject, the level of monokine induced by gamma interferon (CXCL9/MIG) in a sample from a subject, the level of interferon gamma-induced protein-10 (CXCL10/IP10) in a sample from a subject, the level of basic fibroblast growth factor (bFGF) in a sample from a subject, the level of mitochondrial DNA (mtDNA) in a sample from a subject, the level of soluble CD40 ligand (sCD40L) in a subject, the level of transglutaminase 2 in a sample from a subject, gender, age, date of injury, location of injury, presence of abdominal injury, mechanism of injury, wound depth, wound surface area, number of wound debridements, associated injuries, type of wound closure, success of wound closure, requirement for transfusion, total number of blood products transfused, amount of whole blood cells administered to the subject, amount of red blood cells (RBCs) administered to the subject, amount of packed red blood cells (pRBCs) administered to the subject, amount of platelets administered to the subject, level of total packed RBCs, Injury Severity Score (ISS), Abbreviated Injury Scale (AIS) of head, AIS of abdomen, AIS of chest (thorax), Acute Physiology and Chronic Health Evaluation II (APACHE II) score, presence of critical colonization (CC) in a sample from the subject, presence of traumatic brain injury, severity of traumatic brain injury, length of hospital stay, length of intensive care unit (ICU) stay, number of days on a ventilator, disposition from hospital, development of nosocomial infections, sequential organ failure assessment, injury GCS score, Marshall Classification 2 (mild diffuse injury), midline shift based on Rotterdam Computed Tomography (Rott CT)s, temperature, arterial pH, pulse rate, and $FiO_2$.

While one or more of these markers may be applied to any of the one or more clinical outcomes, subsets of these markers may provide more predictive power toward certain clinical outcome, as noted in table 1. The markers in table 1 provide exemplary embodiments of the application of machine learning models. One or more of the markers or a combination of all the markers listed in Table 1 for each respective clinical outcome can be used to predict each of the clinical outcome. One or more includes two or more, three or more, four or more, etc. of the markers. The markers could be obtained from various biological samples and could be proteins or nucleic acids.

TABLE 1

| List of markers and machine learning models tested by clinical outcome | | | |
|---|---|---|---|
| Clinical Outcome | Markers | Machine Learning Models | Performance Metrics |
| Acute Kidney Injury after Trauma Laparotomy | Sequential Organ Failure Assessment (SOFA) score, serum MCP-1, serum VEGF | Logistic Regression, Random Forest | Random Forest: AUC-0.74, Sensitivity-0.82, Specificity-0.61 Logistic Regression: AUC-0.72, Sensitivity-0.77, Specificity-0.64 |
| Acute Kidney Injury in Post-Trauma Combat Patients | ISS, APACHE II, blood transfusion product, nosocomial infection, wound size, and serum levels of IL-2R, IL-6, and MCP-1 | Leave One Out Cross Validation, Backwards Elimination | AUC-0.93, Sensitivity-0.91, Specificity-0.91 |
| Acute Respiratory Distress | APACHE potassium score, injury GCS score verbal, IS head, total SOFA and serum procalcitonin (ProCT) | Bayesian Belief Networks, 5-Fold Cross Validation, Receiver Operating Curve | AUC-0.88, Sensitivity-0.92, Specificity-0.88 |
| Bacteremia | 1. ISS, MIG, IL-6, IL-7, IL-8 2. Serum biomarkers: GCSF, GMCSF, IL-1a, IL-1B, IL-2, IL-4, IL-6, IL-8 VEGF | Backwards Elimination, Leave One Out Cross Validation, Random Forest, Logistic Regression | Model 1: AUC-0.82, Sensitivity-0.79, Specificity-0.74 Model 2: AUC-0.84, Sensitivity-0.78, Specificity-0.78 |
| Heterotopic Ossification in Combat Related Extremity Trauma | IL-8, IL-2R, MIP-1a, GM-CSF, IL-15, IL-12, G-CSF, MIP-1b, IL-1RA, RANTES, | Boruta, Random Forest | AUC-0.82, Sensitivity, 0.88, Specificity-0.61 |
| Heterotopic Ossification from High-Energy Penetrating Traumas | Wound surface area, serum IL8, and effluent IL7 | wound surface area Classification and Regression Tree | AUC-0.83, Sensitivity-0.80, Specificity-0.90 |
| Pneumonia | ISS, AIS chest, cryoprecipitate, FGF-basic, IL-2R, and IL-6 | Backwards Elimination, Random Forest, Logistic Regression, Leave one out cross validation | AUC-0.95 |
| Post-traumatic Sterile inflammation | mtDNA and sCD40L | | $R^2 = 0.18323$, p = 0.042 |
| Sepsis | APACHE GCS verbal score, injury GCS verbal score, 2 penetrating abdominal trauma index variables, serum FGF-basic, and serum IL-6, IL-8 and VEGF | Backwards Elimination, Random Forest | AUC-0.90, Sensitivity-0.88, Specificity-0.77 |

TABLE 1-continued

| | List of markers and machine learning models tested by clinical outcome | | |
|---|---|---|---|
| Clinical Outcome | Markers | Machine Learning Models | Performance Metrics |
| Vasospasm and Mortality Following Severe Traumatic Brain Injury | Marshall Classification 2 (mild diffuse injury), presence of midline shift based on Rott CT, and temperature | Backwards Elimination and Random Forest | Vasospasm: AUC-0.87, Sensitivity-0.85, Specificity-0.81 Mortality-0.90, Sensitivity-0.86, Specificity-0.87 |
| Wound Closure | Serum FGFb, IL-12, EGF, IL-10, IL-1β, VEGF and effluent G-CSF, IL-17, TNF-α, | Boruta, Random Forest | AUC-0.81, Sensitivity-0.70, Specificity-0.40 |

The clinical parameters may include one or more biological effectors and/or one or more non-biological effectors. As used herein, the term "biological effector" or "biomarker" is used to mean a molecule, such as but not limited to, a protein, peptide, a carbohydrate, a fatty acid, a nucleic acid, a glycoprotein, a proteoglycan, etc. that can be assayed. Specific examples of biological effectors can include, cytokines, growth factors, antibodies, hormones, cell surface receptors, cell surface proteins, carbohydrates, etc. More specific examples of biological effectors include interleukins (ILs) such as IL-1α, IL-1β, IL-1 receptor antagonist (IL-1RA), IL-2, IL-2 receptor (IL-2R), IL-3, IL-4, IL-5, IL-6, IL-7, IL-8, IL-10, IL-12, IL-13, IL-15, IL-17, as well as growth factors such as tumor necrosis factor alpha (TNFα), granulocyte colony stimulating factor (G-CSF), granulocyte macrophage colony stimulating factor (GM-CSF), interferon alpha (IFN-α), interferon gamma (IFN-γ), epithelial growth factor (EGF), basic endothelial growth factor (bEGF), hepatocyte growth factor (HGF), vascular endothelial growth factor (VEGF), and chemokines such as monocyte chemoattractant protein-1 (CCL2/MCP-1), macrophage inflammatory protein-1 alpha (CCL3/MIP-1α), macrophage inflammatory protein-1 beta (CCL4/MIP-1β), CCL5/RANTES, CCL11/eotaxin, monokine induced by gamma interferon (CXCL9/MIG) and interferon gamma-induced protein-10 (CXCL10/IP10). In embodiments, the biological effectors are soluble. In embodiments, the biological effectors are membrane-bound, such as a cell surface receptor. In embodiments, the biological effectors are detectable in a fluid sample of a subject such as serum, wound effluent, and/or plasma.

As used herein, the term non-biological effector is a clinical parameter that is generally considered not to be a specific molecule. Although not a specific molecule, a non-biological effector may nonetheless still be quantifiable, either through routine measurements or through measurements that stratify the data being assessed. For example, number or concentrate of red blood cells, white blood cells, platelets, coagulation time, blood oxygen content, etc. would be a non-biological effector component of the risk profile. All of these components are measurable or quantifiable using routine methods and equipment. Other non-biological components include data that may not be readily or routinely quantifiable or that may require a practitioner's judgment or opinion. For example, wound severity may be a component of the risk profile. While there may be published guidance on classifying wound severity, stratifying wound severity and, for example, assigning a numerical value to the severity, still involves observation and, to a certain extent, judgment or opinion. In some instances the quantity or measurement assigned to a non-biological effector could be binary, e.g., "0" if absent or "1" if present. In other instances, the non-biological effector aspect of the risk profile may involve qualitative components that cannot or should not be quantified.

In embodiments, the mechanism of injury is a clinical parameter. As used herein, the phrase "mechanism of injury" means the manner in which the subject received an injury and may fall into one of three categories: blast, crush, or gunshot wound (GSVV). A blast injury is a complex type of physical trauma resulting from direct or indirect exposure to an explosion. Blast injuries may occur, for example, with the detonation of high-order explosives as well as the deflagration of low order explosives. Blast injuries may be compounded when the explosion occurs in a confined space. A crush injury is injury by an object that causes compression of the body. Crush injuries are common following a natural disaster or after some form of trauma from a deliberate attack. A GSW is an injury that occurs when a subject is shot by a bullet or other sort of projectile from a firearm. Abdominal Trauma Index Scores are scores that are based on several different methods of assessing the level of trauma that occurs to the abdominal region. For examples, Abdominal Trauma Index Scores may comprise one or more of, but is not limited to the Abdominal Trauma Index, the Penetrating Abdominal Trauma Index, the Injury Severity Score. The Injury GCS Score Verbal is the subset of the GCS score wherein verbal response is scored based on the following criteria: oriented (5 points), confused conversation but able to answer questions (4 points), inappropriate word choice (3 points), incomprehensible speech (2 points), no response (1 point). The Sequential Organ Failure Assessment (SOFA) score measures the number and severity of organ dysfunction in six organ systems (respiratory, coagulatory, liver, cardiovascular, renal, and neurological). As such, the SOFA score can measure individual or aggregate organ dysfunction.

Levels of the clinical parameters can be assayed, detected, measured, and/or determined in a sample taken or isolated from a subject. "Sample" and "test sample" are used interchangeably herein.

Examples of test samples or sources of clinical parameters include, but are not limited to, biological fluids and/or tissues isolated from a subject or patient, which can be tested by the methods of the present application described herein, and include but are not limited to whole blood, peripheral blood, serum, plasma, cerebrospinal fluid, wound effluent, urine, amniotic fluid, peritoneal fluid, pleural fluid, lymph fluids, various external secretions of the respiratory, intestinal, and genitourinary tracts, tears, saliva, white blood cells, solid tumors, lymphomas, leukemias, myelomas, and combinations thereof. In particular embodiments, the sample is a serum sample, wound effluent, or a plasma sample.

In embodiments, the clinical parameters are one or more of biomarkers, administration of blood transfusion products (blood products), administration of cryoprecipitate, and injury severity scores. In embodiments, the clinical parameters of a subject are selected from one or more, two or more, three or more, four or more, five or more, six or more, seven or more, eight or more, nine or more, 10 or more, 11 or more, 12 or more, 13 or more, 14 or more, 15 or more, 16 or more, 17 or more, 18 or more, 19 or more, 20 or more, 21 or more, 22 or more, 23 or more, 24 or more, 25 or more, 26 or more, 27 or more, 28 or more, 29 or more, 30 or more, 31 or more, 32 or more, 33 or more, 34 or more, 35 or more, 36 or more, 37 or more, 38 or more, 39 or more, 40 or more, 41 or more, 42 or more, 43 or more, 44 or more, or 45 of the clinical parameters mentioned here in.

In embodiments of the methods disclosed herein, the clinical parameters are selected from one or more of AIS of head, AIS of abdomen, amount of platelets administered to the subject, level of total packed RBCs administered to the subject, summation of all blood products administered to the subject, level of interferon gamma induced protein 10 (IP-10) in a serum sample from the subject, level of interleukin-10 (IL-10) in a serum sample from the subject, and level of monocyte chemoattractant protein 1 (MCP-1) in a serum sample from the subject.

As used herein, the term "summation of all blood products administered to the subject" refers to a value reflecting the total amount of blood products administered to the subject. Blood products include but are not limited to whole blood, platelets, red blood cells, packed red blood cells, and serum. In embodiments, this value reflects the total amount of blood products needed to stabilize the subject following hemorrhage. Stabilization refers to homeostasis achieved in the subject and is defined as either achieving an equilibrium between bleeding or a complete cessation of hemorrhage in the subject.

As used herein, the term "AIS" refers to the abbreviated injury scale, a well-known parameter in the art used routinely in clinics to assess severity of wounds or injuries. In embodiments, an AIS of 1 is a minor injury, an AIS of 2 is a moderate injury, and AIS of 3 is a serious injury, an AIS of 4 is a severe injury, an AIS of 5 is a critical injury, and an AIS of 6 is an nonsurvivable injury.

As used herein, the term critical colonization (or "CC") is a measure of CFU that the subject has in serum and/or tissue for at least one wound when initially examined by the attending physician. For example, if a subject has CFU of $1 \times 10^5$ per ml of serum, or if at least one wound has CFU of $1 \times 10^5$ per mg of tissue, the subject is said to be "positive" for CC. If the total serum CFU or no single wound has CFU of at least $1 \times 10^5$ the subject is said to be "negative" for CC.

As used herein, assessing an injury such as an abdominal injury and/or a head injury, for the purposes of using these clinical parameters in the systems and methods described herein, means determining the degree or extent of injury, as reflected in an AIS score of 1-6.

In various embodiments, systems, methods, and a non-transitory computer-readable medium of the present disclosure can execute a process by which data is aggregated about one or more subjects, machine learning algorithms perform data-mining procedures, pattern recognition, intelligent prediction, and other artificial intelligence procedures, such as for enabling diagnostic predictions based on clinical data. Machine learning algorithms are increasingly being implemented to reveal knowledge structures that guide decisions in conditions of limited certainty which can lead to improved decision making. Using manual techniques or traditional algorithmic approaches, this would not be possible because of the large number of data points involved. However, in order to use machine learning algorithms effectively, a machine learning engine comprising a specific sequence of approaches and comparisons of models implemented by machine learning algorithms may be required in order to get optimal results out of existing data.

Constructing such a machine learning engine and executing these machine learning algorithms can improve the performance of diagnostic prediction technology. These improvements may include, but are not limited to by increasing accuracy, selectivity, and/or specificity of models used to perform the diagnostic predictions. Therefore, such an engine can improve decision-making for and delivery of treatments to subjects. While various machine learning algorithms can be used for such purposes, generating a machine learning engine with desired performance characteristics can be highly domain-specific, requiring rigorous modeling, testing, and validation to select appropriate algorithms (or combinations thereof) and the parameters modeled with the algorithms to generate the machine learning system.

In embodiments, the machine learning engine may be constructed to include five major components: (1) initial data exploration, (2) variable and/or feature selection, (3) classification, (4) model selection via validation, (5) deployment and self-improvement. It will be understood by those possessing ordinary skill in the art that these stages may not be discrete entities and there may be overlap between them, and that the output from each stage may be used to inform, calibrate, and/or improve other stages of the engine and the machine learning engine.

The initial data stage may include data preparation. Data preparation may include cleaning data (e.g., searching for outlying data, applying missing data algorithms, alter data formats), transforming data, selecting subsets of records and—in case of data sets with large numbers of variables ("fields or dimensions"). The data on which data preparation is performed may be referred to as training data.

In embodiments, data preparation can include executing pre-processing operations on the data. For example, missing data may be handled through the execution of imputation algorithms that interpolate and/or estimate missing values. One example of imputation involves generating a distribution (e.g. Gaussian, Poisson, binomial, zero-inflation, beta, pert) of available data for a clinical parameter having missing data, and interpolating values for the missing data based on the distribution.

The variable selection stage involves performing variable selection operations (e.g., feature selection, parameter selection), to bring the number of variables to a manageable and appropriate range (depending on the statistical methods which are being considered). In many supervised learning problems, variable selection can be important for a variety of reasons including generalization performance, running time requirements and constraints and interpretational issues imposed by the problem itself (e.g., understanding direction of causality, removing known confounders). The data on which the variable selection is performed may be referred to as training data. Given that the performance of machine learning algorithms can depend strongly on the quality of the training data used to train the algorithms, variable selection and other data preparation operations can be highly significant for ensuring desired performance.

In embodiments, variable selection can include executing supervised machine learning algorithms, such as constraint-based algorithms, constrain-based structure learning algorithms, and/or constraint-based local discovery learning algorithms. Variable selection can be executed to identify a subset of variables in the training data which have desired predictive ability relative to a remainder of the variables in the training data, enabling more efficient and accurate predictions using a model generated based on the selected variables. In embodiments, variable selection is performed using machine learning algorithms from the "bnlearn" R package, including but not limited to the Grow-Shrink ("gs"), Incremental Association Markov Blanket ("iamb"), Fast Incremental Association ("fast.iamb"), Max-Min Parents & Children ("mmpc"), or Semi-Interleaved Hiton-PC ("si.hiton.pc") algorithms. R is a programming language and software environment for statistical computing. It will be appreciated that various other implementations of such machine learning algorithms (in R or other environments such as Python) may be used to perform variable selection and other processes described herein. Variable selection can search for a smaller dimension set of variables that seek to represent the underlying distribution of the full set of variables, which attempts to increase generalizability to other data sets from the same distribution.

In embodiments, variable selection is performed to search the training data for a subset of variables which are used as nodes of Bayesian networks. A Bayesian network (e.g., belief network, Bayesian belief network) is a probabilistic model representing a set of variables and their conditional dependencies using a directed acyclic graph. For example, in the context of diagnostic prediction, variable selection can be used to select variables from the training data to be used as nodes of the Bayesian network; given values for the nodes for a specific subject, a prediction of a diagnosis for the subject can then be generated. While Bayesian networks are contemplated, many other variable selection algorithms are contemplated, including, but not limited to: neural networks, step-wise regression, support vector machines. Backwards Elimination begins with all the variables and removes variables in a backwards, stepwise manner. At each step the model is tested to see if it is improved by the removal of a variable. The removal of variables ends when removing variables no longer improves the model and the optimal selection of variables is achieved. Exemplary embodiments of variable selection machine learning models that have proven to improve prediction based on the present markers and training data are listed by clinical outcome in Table 1.

The classification stage involves the task of generalizing a known structure and applying it to new data. Classification algorithms can include, but are not limited to linear discriminant analysis, classification and regression trees/decision tree learning/random forest modeling, nearest neighbor, support vector machine, logistic regression, generalized linear models, Naive Bayesian classification, and neural networks, among others. In embodiments, classification algorithms can be used from the train function of the R caret package, including but not limited to linear discriminant analysis (lda), classification and regression trees (cart), k-nearest neighbors (knn), support vector machine (svm), logistic regression (glm), random forest (rf), generalized linear models (glmnet) and/or naïve Bayes (nb). These classification algorithms are used to form predictions of the presence (i.e., is the clinical outcome present or not) or development (i.e., will the clinical outcome develop or not) of a clinical outcome. While these classification algorithms are disclosed, many others are contemplated, including k-means cluster, non-linear clustering, boosted trees, mixture models, and/or OPTICS algorithms.

For example, in one variant of a classification machine learning model Naïve Bayesian algorithms can apply Bayes' theorem to predict outcomes based on values of variables, such as values of the variables identified using variable selection. The model is called "naïve" due to the assumption that each of the variables is independently associated with having one or more clinical outcomes. While it may be more realistic for there to be a joint probability for the variables when performing predictions, the naïve approach may provide performance characteristics desirable for the diagnostic prediction system being generated. A naïve Bayes model can be trained by calculating a relationship between values of each variable and the corresponding outcome(s) represented in the training data. For example, in a diagnostic prediction system for a clinical outcome, values of each variable may be associated with the outcomes of whether or not the particular clinical outcome is present. In embodiments, the relationship may be calculated using a normal distribution for the values of the variables, such that the normal distribution can be used to determine a probability that each variable may have a specified value in the case of (1) the clinical outcome being present, or (2) the clinical outcome not being present. Then, when executing the trained naïve Bayes to predict the presence of the particular disease for a subject, a probability can be calculated, for each value of each variable, that the variable would have that value given that the particular disease is present in the subject; similarly, a probability can be calculated, for each value of each variable, that the variable would have that value given that the clinical outcome is not present in the subject. The probabilities for each case can be combined, and then compared to generate a prediction as to whether the clinical outcome is present in the subject.

In a separate variant of a classification machine learning model, a neural network includes a plurality of layers each including one or more nodes, such as a first layer (e.g., an input layer), a second layer (e.g., an output layer), and one or more hidden layers. The neural network can include characteristics such weights and biases associated with computations that can be performed between nodes of layers. For example, a node of the input layer can receive input data, perform a computation on the input data, and output a result of the computation to a hidden layer. The hidden layer may receive outputs from one or more input layer nodes, perform a computation on the received output(s), and output a result to another hidden layer, or to the output layer. The weights and biases can affect the computations performed by each node and can be manipulated by an algorithm executing the neural network, such as an optimization algorithm being used to train the neural network to match training data. Neural networks describe a generalized approach to classification and many different variants of neural networks may be used, including, but not limited to: convolutional neural networks, deep belief networks, deep reservoir computing, restricted Boltzmann machines, deep stacking networks, tensor deep stacking networks, and/or hierarchical-deep models.

In another variant of a classification machine learning model, a random forest mode may be utilized. A random forest can include a "forest" of a large number of decision trees, such as on the order of $10^2$ to $10^5$ decision trees. The number of decision trees may be selected by calculating an OOB error (the mean prediction error on each training sample, using only the trees that did not have each training sample in their randomly sampled set of training data, as discussed below) for the resulting random forest model. In embodiments, the number of decision trees used may be several hundred trees, which can improve computational performance of the machine learning systems by reducing the number of calculations needed to execute the random forest model. The two chief draws of the random forest are that it does not require the data to be either normally distribution or transformed and that the algorithm requires little tuning, which is advantageous when updating data sets, and its numerical process includes cross validation precluding the need for post model-building cross validation.

In embodiments, each random forest decision tree is generated by bootstrap aggregating ("bagging"), where for each decision tree, the training data is randomly sampled with replacement to generate a randomly sampled set of training data, and then the decision tree is trained on the randomly sampled set of training data. In embodiments, where variable selection is performed prior to generated the random forest model, the training data is sampled based on the reduced set of variables from variable selection (as opposed to sampling based on all variables).

To perform a prediction given values of variables for a subject, each decision tree is traversed using the given values until a decision rule is reached that is followed by terminal nodes (e.g., presence of disease in the subject, no presence of disease in the subject). The outcome from the decision rule followed by the terminal nodes is then used as the outcome for the decision tree. The outcomes across all decision trees in the random forest model are summed to generate a prediction regarding the subject.

Regression analysis attempts to find a function which models the data with the least error. Regression analysis can be used for prediction, as the function can be used to predict a value for a dependent variable given value(s) for independent variable(s). In some examples, logistic regression can be used to classify the presence or absence of a clinical outcome. Regressions can involve linear regressions, which involves a linear approach to modeling the relationship between a dependent variable and one or more independent variables, or they can involve non-linear regressions in which are regression in which the dependent or criterion variables are modeled as a non-linear function of model parameters and one or more independent variables.

Model selection includes but is not limited to considering the various machine learning algorithms and models and selecting the best one based on predictive performance. Predictive performance can correspond to explaining the variability in question and producing stable results across samples. This process requires a systematic and elaborate approach to screening a multitude of models across various metrics and comparing results across models, outcomes, and populations. There are a variety of techniques developed to achieve that goal—many of which are based on so-called "competitive evaluation of models", that is, applying different models to the same data set and then comparing their performance to choose the best model. These techniques—which are often considered the core of predictive machine learning—can include: bagging (voting, averaging), boosting, stacking (stacked generalizations), and meta-learning. Validation can include comparing the output of a selected model to validation data. For example, a portion of the training data can be held separately from that which is used to train the model, and then can be used to confirm the performance characteristics of the trained model. The portion of training data that can be held separately from that which is used to train the model can include 0.1-1% of the data, 1-5% of the data, 1-10% of the data, 1-15% of the data, 1-20% of the data, 1-25% of the data, 1-30% of the data, 1-35% of the data, 1-40% of the data, 1-45% of the data, 1-50% of the data, 1-55% of the data, 1-60% of the data, 1-75% of the data, 1-80% of the data, 1-85% of the data, 1-90% of the data, 1-95% of the data, or 1-99% of the data.

In embodiments a comparison of machine learning algorithms (and combinations thereof) may be useful. Many application scenarios do not have single models, but multiple, related ones. Some typical examples are machine learning algorithms trained based on data derived at different points in time or in different subsets of the data, e.g., production quality data from different production sites. Another common case is representing the same data with machine learning algorithms on different types of machine learning algorithms in order to capture different aspects of the data. In all these cases, not only the individual data mining models are of interest, but also similarities and differences between them. Such differences may tell, for instance, how production quality and dependencies develop over time, how machine learning algorithms of different types differ in their ways of representing different products produced at the same facility or, how the production facilities differ between each other. Current examples of classification machine learning that have proven to improve prediction based on the present markers and training data are listed by clinical outcome in Table 1. While the models in Table 1 reflect the most current understanding and application of machine learning models, as the machine learning engine and prediction engine is trained on more data and updated models, the markers and machine learning models that best fit each clinical outcome may change.

Machine learning algorithms (and combinations thereof) can be compared using performance metrics. The performance metrics may be selected based on the intended application of the machine learning algorithms (and the predictive models created using the machine learning algorithms). For diagnostic prediction models, the performance metrics can include but is not limited to Kappa score, Accuracy score, sensitivity, specificity, total, positive class, and negative class out-of-bag (OOB) error estimates, receiver operator characteristic curves (ROCs), areas under curve (AUCs), confusion matrices, Vickers and Elkins' Decision Curve Analysis (DCA), or other measures of the performance of the machine learning algorithms The Kappa score represents a comparison of an observed accuracy of the diagnostic prediction model to an expected accuracy. For example, the Kappa score measures how closely the diagnostic prediction model matches training data (e.g., the relationships between variables and the corresponding outcomes known in the training data), controlling for the accuracy of a random classifier as measured by the expected accuracy.

The sensitivity measures a proportion of positive results from the prediction that are correctly identified as such. As such, the sensitivity can quantify the avoidance of false negatives. The specificity measures a proportion of negative results from the prediction that are correctly identified as such.

OOB measures prediction error in random forest and other machine learning techniques that rely on bootstrapping to sub-sample training data. The OOB error analysis can be used to show how the variable selected models can improve the OOB error (predictive performance) for the positive class.

The ROC curve is a plot of true positive rate (sensitivity) as a function of false positive rate (specificity). The AUC represents the area under the ROC curve, wherein a 1 represents a perfect model fit with 100% sensitivity and specificity. For example, model performance can be further assessed using the plot.roc command in R to compute the Receiver Operator Characteristic Curves (ROC) and area under curve (AUC).

Decision Curve Analysis (DCA) can be used to calculate the net benefit of treatment based on the diagnoses predicted by the diagnostic prediction models, as compared to baseline treatment methodologies such as assuming that all patients are test positive and therefore treating everyone, or assuming that all patients are test negative and therefore offering treatment to no one. The DCA curve plots the net benefit of the diagnostic prediction model as a function of a threshold probability, the threshold probability being a value at which the subject would opt for treatment given the relative harms of false positive predictions. DCA is used to compare various predictive and diagnostic paradigms in terms of net benefit to the patient. A typical DCA analysis will compare the null model, treat no one, to various alternative models, such as "treat-all" or treat according to the guidance of models built on biomarker predictors. DCA analysis can be interpreted as showing positive net-benefit to the patient if the decision curve for a particular model is above the null model (x axis), and to the right of the "treat-all" model. Net-benefit is defined mathematically as a summation of model performance (for instance propensity to predict false positive or false negatives) over a series of predictive threshold cutoffs and the respective sensitivity/specificity at those thresholds. The threshold cutoffs could be thought of as the point at which a decision to treat would be made given the relative harms and benefits of treating given the uncertainty of the prediction at that threshold. This analysis demonstrates the threshold cutoffs where the predictive models are most useful to the patient. The dca R command from the Memorial Sloan Kettering Cancer Center website, www.mskcc.org, can be used to compute the Decision Curve Analysis (DCA).

Deployment and self-improvement can include using the model selected as the best model in the previous stage and deploying it to a prediction engine. This prediction engine takes in new data, applies the selected model, and generates predictions or estimations of the expected one or more clinical outcomes. For example, the selected model can be executed using clinical data specific to a particular subject in order to predict the expected outcome for the particular subject. In embodiments, the clinical data for the particular subject can be used to update the machine learning engine, particularly after confirming whether or not the disease is present in the particular subject. As such, the machine learning engine adopts an iterative, self-improvement process upon deployment.

In embodiments, the systems and methods described herein for generating predictive models for predicting subject-specific pneumonia outcomes involve the execution of two main steps: variable selection and multi-class classification. An advantage of variable selection is that variable selection can search for a smaller dimension set of variables that seek to represent the underlying distribution of the full set of variables, which attempts to increase generalizability to other data sets from the same distribution. In embodiments, such as where the datasets are relatively small, computational time may not be a consideration. Since variable selection is based on a better representation of the underlying distribution of the full variables set, in theory, they should be more generalizable and less susceptible to over fitting.

In building machine learning engines to predict clinical outcomes, it is typically unfeasible and unwarranted to provide the machine learning algorithms with an exhaustive list of clinical parameters which may be relevant to the clinical outcomes being predicted. For example, with very large lists of clinical parameters, there may be significant noise, multicollinearity, large amounts of missing data, and other opportunities for introducing errors which can adversely affect the ability of the machine learning algorithms to generate predictive models (by performing variable selection and classification) which meet desired performance metrics.

In some situations, the number of clinical parameters may be on the order of 5000-50000 variables, from which the machine learning solutions will have to perform variable selection and other operations. To do so would require incredibly large computing resources which are not readily available, making such processes virtually impossible. Additionally, even if such resources were available, the opportunities for introducing error in the resulting solutions would counteract any added benefit from considering all variables.

In some embodiment, over 7000 initial clinical and non-clinical parameters are available regarding the subjects that could potentially be used to train the machine learning solutions. These clinical parameters fall into a wide variety of categories, such as demographics, wound type, wound mechanism, wound location, fracture characteristics, administration of blood products, injury severity scores, treatment(s), tobacco usage, activity levels, surgical history, nutrition, serum protein expression, wound effluent protein expression, tissue bacteriology, mRNA expression, and Raman spectroscopy. In embodiments, these categories, using expert knowledge, the following are selected for usage with the machine learning solutions disclosed herein: serum protein expression, administration of blood products, and injury severity scores. The expert selection process is based upon many criteria, including, but not limited to established causal mechanisms of action for disease processes or clinical outcomes, diagnostic algorithms. The expert selection process is important for distilling the many possible parameters to the minimum number that will result in the strongest predictive power.

In embodiments, clinical parameters that fall within the serum protein expression include but are not limited to any one or more of level of interleukin-1α (IL-1α) in a sample from the subject, level of interleukin-Iβ (IL-Iβ) in a sample from the subject, level of interleukin-1 receptor agonist (IL-1RA) in a sample from the subject, level of interleukin-2 (IL-2) in a sample from the subject, level of interleukin-2 receptor (IL-2R) in a sample from the subject, level of interleukin-3 (IL-3) in a sample from the subject, level of interleukin-4 (IL-4) in a sample from the subject, level of interleukin-5 (IL-5) in a sample from the subject, level of interleukin-6 (IL-6) in a sample from the subject, level of interleukin-7 (IL-7) in a sample from the subject, level of interleukin-8 (IL-8) in a sample from the subject, level of interleukin-10 (IL-10) in a sample from the subject, level of interleukin-12 (IL-12) in a sample from the subject, level of interleukin-13 (IL-13) in a sample from the subject, level of interleukin-15 (IL-15) in a sample from the subject, level of interleukin-17 (IL-17) in a sample from the subject, level of tumor necrosis factor alpha (TNF-α) in a sample from the subject, level of granulocyte colony stimulating factor (G-CSF) in a sample from the subject, level of granulocyte macrophage colony stimulating factor (GM-CSF) in a sample from the subject, level of interferon alpha (IFN-α) in a sample from the subject, level of interleukin-8 (IL-8) in a sample from the subject, level of interleukin-10 (IL-10) in a sample from the subject, level of interferon gamma (IFN-γ) in a sample from the subject, level of epithelial growth factor (EGF) in a sample from the subject, level of basic epithelial growth factor (bFGF) in a sample from the subject, level of hepatocyte growth factor (HGF) in a sample from the subject, the level of vascular endothelial growth factor (VEGF) in a sample from a subject, the level of monocyte chemoattractant protein-1 (CCL2/MCP-1) in a sample from a subject, the level of macrophage inflammatory protein-1 alpha (CCL3/MIP-Iα) in a sample from a subject, the level of macrophage inflammatory protein-1 beta (CCL4/MIP-Iβ) in a sample from a subject, the level of CCL5/RANTES in a sample from a subject, the level of CCL11/eotaxin in a sample from a subject, the level of monokine induced by gamma interferon (CXCL9/MIG) in a sample from a subject, the level of interferon gamma-induced protein-10 (CXCL10/I P10) in a sample from a subject, the level of basic fibroblast growth factor (bFGF) in a sample from a subject, the level of mitochondrial DNA in a sample from a subject, the level of soluble CD40 ligand (sCD40L) in a subject, the level of transglutaminase 2 in a sample from a subject, among others.

In embodiments, clinical parameters that fall within the administration of blood products category include amount of whole blood cells administered to the subject, amount of red blood cells (RBCs) administered to the subject, amount of packed red blood cells (pRBCs) administered to the subject, amount of platelets administered to the subject, summation of all blood products administered to the subject, and/or level of total packed RBCs, among others.

In embodiments, clinical parameters that fall within the injury severity scores category include Injury Severity Score (ISS), Abbreviated Injury Scale (AIS) of abdomen, AIS of chest (thorax), AIS of extremity, AIS of face, AIS of head, and/or AIS of skin, among others.

The machine learning solutions described herein can execute variable selection on the clinical parameters within the identified categories to generate predictive models for predicting one or more clinical outcomes, wherein the one or more clinical outcomes may comprise acute kidney injury, acute respiratory distress, bacteremia, heterotopic ossification, pneumonia, post-traumatic sterile inflammation, sepsis, wound closure, or vasospasm and/or mortality following traumatic brain injury.

Referring now to FIG. 1, the process of a Machine Learning Engine 204 and it's components are shown according to an embodiment of the present disclosure. The machine learning engine starts with training data 102 and executes variable selection 118 in a variable selection engine 120, then executes classification 126 in a classification engine, and the model(s) is/are deployed for prediction 134 in a prediction engine 136.

In embodiments, the training data 102 comprises clinical parameters 104 (e.g., mechanism of injury data 106, biomarker data 108, index/score data 110, and diagnostic imaging data 112), clinical outcome data 114, and administrative health data 116.

In embodiments, the mechanism of injury data 106 may includes, but is not limited to one or more of: blast wound, crush wound, gunshot wound, impalement wound. A blast injury is a complex type of physical trauma resulting from direct or indirect exposure to an explosion. Blast injuries may occur, for example, with the detonation of high-order explosives as well as the deflagration of low order explosives. Blast injuries may be compounded when the explosion occurs in a confined space. A crush injury is injury by an object that causes compression of the body. Crush injuries are common following a natural disaster or after some form of trauma from a deliberate attack. A gunshot wound is an injury that occurs when a subject is shot by a bullet or other sort of projectile from a firearm. An impalement wound is an injury involving pierced or transfixed with a sharp object.

In embodiments, the biomarker data 108 may include, but is not limited to one or more of interleukin-1α (IL-1α) in a sample from the subject, level of interleukin-Iβ (IL-Iβ) in a sample from the subject, level of interleukin-1 receptor agonist (IL-1RA) in a sample from the subject, level of interleukin-2 (IL-2) in a sample from the subject, level of interleukin-2 receptor (IL-2R) in a sample from the subject, level of interleukin-3 (IL-3) in a sample from the subject, level of interleukin-4 (IL-4) in a sample from the subject, level of interleukin-5 (IL-5) in a sample from the subject, level of interleukin-6 (IL-6) in a sample from the subject, level of interleukin-7 (IL-7) in a sample from the subject, level of interleukin-8 (IL-8) in a sample from the subject, level of interleukin-10 (IL-10) in a sample from the subject, level of interleukin-12 (IL-12) in a sample from the subject, level of interleukin-13 (IL-13) in a sample from the subject, level of interleukin-15 (IL-15) in a sample from the subject, level of interleukin-17 (IL-17) in a sample from the subject, level of tumor necrosis factor alpha (TNF-α) in a sample from the subject, level of granulocyte colony stimulating factor (G-CSF) in a sample from the subject, level of granulocyte macrophage colony stimulating factor (GM-CSF) in a sample from the subject, level of interferon alpha (IFN-α) in a sample from the subject, level of interleukin-8 (IL-8) in a sample from the subject, level of interleukin-10 (IL-10) in a sample from the subject, level of interferon gamma (IFN-γ) in a sample from the subject, level of epithelial growth factor (EGF) in a sample from the subject, level of basic epithelial growth factor (bFGF) in a sample from the subject, level of hepatocyte growth factor (HGF) in a sample from the subject, the level of vascular endothelial growth factor (VEGF) in a sample from a subject, the level of monocyte chemoattractant protein-1 (CCL2/MCP-1) in a sample from a subject, the level of macrophage inflammatory protein-1 alpha (CCL3/MIP-Ia) in a sample from a subject, the level of macrophage inflammatory protein-1 beta (CCL4/M I P-Iβ) in a sample from a subject, the level of CCL5/RANTES in a sample from a subject, the level of CCL11/eotaxin in a sample from a subject, the level of monokine induced by gamma interferon (CXCL9/MIG) in a sample from a subject, the level of interferon gamma-induced protein-10 (CXCL10/I P10) in a sample from a subject, the level of basic fibroblast growth factor (bFGF) in a sample from a subject, the level of mitochondrial DNA in a sample from a subject, the level of soluble CD40 ligand (sCD40L) in a subject, the level of transglutaminase 2 in a sample from a subject, gender, age, date of injury, location of injury, presence of abdominal injury, mechanism of injury, wound depth, wound surface area, number of wound debridements, associated injuries, type of wound closure, success of wound closure, requirement for transfusion, total number of blood products transfused, amount of whole blood cells administered to the subject, amount of red blood cells (RBCs) administered to the subject, amount of packed red blood cells (pRBCs) administered to the subject, amount of platelets administered to the subject, level of total packed RBCs, Injury Severity Score (ISS), Abbreviated Injury Scale (AIS) of head, AIS of abdomen, AIS of chest (thorax), Acute Physiology and Chronic Health Evaluation II (APACHE II) score, presence of critical colonization (CC) in a sample from the subject, presence of traumatic brain injury, severity of traumatic brain injury, length of hospital stay, length of intensive care unit (ICU) stay, number of days on a ventilator, disposition from hospital, development of nosocomial infections, sequential organ failure assessment, injury GCS score, Marshall Classification 2 (mild diffuse injury), midline shift based on Rotterdam computed tomography temperature, arterial pH, pulse rate, and $FiO_2$.

In embodiments, the index/score data 110 may include, but is not limited to one or more of: Injury Severity Score, Abbreviated Injury Scale, Glasgow Coma Scale (GCS), or Revised Trauma Scale (RTS). While these index/data score data 110 are enumerated, many others are contemplated.

In embodiments, the diagnostic imaging data 112 may include, but is not limited to one or more of: X-ray, computed tomography scan, magnetic resonance imaging, angiography, ultrasound, or PET scan. While these diagnostic imagine data 112 are enumerated, many others are contemplated.

In embodiments, the clinical outcome data 114 may include, but is not limited to one or more of: acute kidney injury, acute respiratory distress, bacteremia, heterotopic ossification, pneumonia, post-traumatic sterile inflammation, sepsis, wound closure, or vasospasm and/or mortality following traumatic brain injury.

In embodiments, the administrative health data 116, may include, but is not limited to one or more of: gender, age, date of injury, location of injury, presence of abdominal injury, wound depth, wound surface area, number of wound debridements, associated injuries, type of wound closure, success of wound closure, requirement for transfusion, total number of blood products transfused, amount of whole blood cells administered to the subject, amount of RBCs administered to the subject, amount of PRBCs administered to the subject, amount of platelets administered to the subject, level of total PRBCs, presence of critical colonization (CC) in a sample from the subject, presence of traumatic brain injury, severity of traumatic brain injury, length of hospital stay, length of intensive care unit (ICU) stay, number of days on a ventilator, disposition from hospital, or development of nosocomial infections. While these administrative health data 116 are enumerated, many others are contemplated.

In embodiments, the variable selection engine 120 executes a series of variable selection machine learning models 122. The machine learning models 122 include, but are not limited to one or more of: constraint-based algorithms, constraint-based structure learning algorithms, and/or constraint-based local discovery learning algorithms. For example, the machine learning engine 204 can execute machine learning algorithms from the "bnlearn" R package, including but not limited to the Grow-Shrink ("gs"), Incremental Association Markov Blanket ("iamb"), Fast Incremental Association ("fast.iamb"), Max-Min Parents & Children ("mmpc"), or Semi-Interleaved Hiton-PC ("si.hiton.pc") algorithms. While these variable selection are enumerated, many others are contemplated. In embodiments, the variable selection results 124 of the variable selection machine learning models 122 are compared and the top performing variables are selected.

Classification 126 occurs in the classification engine 128, wherein classification machine learning models 130 are used to predict one or more clinical outcomes based on the clinical parameters selected during variable selection. Classification machine learning models can include, but are not limited to linear discriminant analysis, classification and regression trees/decision tree learning/random forest modeling, nearest neighbor, support vector machine, logistic regression, generalized linear models, naive Bayesian classification, and neural networks, among others. In embodiments, classification algorithms can be used from the train function of the R caret package, including but not limited to linear discriminant analysis (lda), classification and regression trees (cart), k-nearest neighbors (knn), support vector machine (svm), logistic regression (glm), random forest (rf), generalized linear models (glmnet) and/or naïve Bayes (nb). These classification algorithms are used to form predictions of the presence (i.e., is the clinical outcome present or not) or development (i.e., will the clinical outcome develop or not) of a clinical outcome. While these classification algorithms are disclosed, many others are contemplated, including k-means cluster, non-linear clustering, boosted trees, mixture models, and/or OPTICS algorithms. The classification machine learning models 130 may be executed by identifying first values of clinical parameters in the training database 105 corresponding to each subset of model parameters, and generating predictions of one or more clinical outcomes using the identified first values.

The machine learning engine 204 can use the predictions of clinical outcomes to calculate performance metrics that are derived from the classification results 132. For example, the machine learning engine 204 can calculate a performance metric for each combination of (i) a subset of model parameters (selected by each variable selection machine learning model 122) and (ii) a classification machine learning model 130 used to generate the predictions of one or more clinical outcomes. The performance metrics can represent the ability of each combination to predict one or more clinical outcomes.

The classification engine 128 can calculate a performance metric including, but not limited to one or more a Kappa score, a sensitivity, or a specificity. The Kappa score indicates a comparison of an observed accuracy of the combination of the subset of model parameters and the classification machine learning model 130 to an expected accuracy. In embodiments, the classification engine 128 can generate an ROC curve based on the sensitivity and the specificity. The classification engine 128 can also calculate an AUC based on the ROC curve. In embodiments, the candidate classification machine learning model 130 can be evaluated by further performance metrics. For example, the candidate classification machine learning model 130 can be evaluated based on Accuracy, No Information Rate, positive predictive value and negative predictive value.

The classification engine 128 can apply various policies, heuristics, or other rules based on the performance metric(s) to select a candidate classification machine learning model 130 (and corresponding subset of model parameters selected by one of the variable selection machine learning models 122). For example, values for each performance metric can be compared to respective threshold values, and a classification machine learning model 130 can be determined to be a candidate classification machine learning model 130 (or a potential candidate) responsive to the value for the performance metric exceeding the threshold. The classification engine 128 can assign weights to each performance metric to calculate a composite performance metric. The classification engine 128 can evaluate performance metrics in a specified order.

In embodiments, the classification engine 128 selects the candidate classification machine learning model 130 and corresponding subset of model parameters based on the rule: identify the combination having (1) a highest Kappa score; subsequently, (2) a highest sensitivity; and (3) subsequently, a specificity greater than a threshold specificity.

The classification engine 128 can execute decision curve analysis (DCA) to evaluate the performance of the candidate classification machine learning model 130 and/or with confusion matrices. DCA can be used to assess the net benefit of using the candidate classification machine learning model 130 in a clinical setting as compared to a null model, a treat no one paradigm, or a "treat-all" intervention paradigm. The DCA can be executed to validate the performance of the candidate classification machine learning model 130, and/or to select the candidate classification machine learning model 130 from amongst several classification machine learning model 130 having similar performance under other performance metrics.

The classification engine 128 can be executed in multiple iterations. For example, the data of the training database 102 can be run through the variable selection and classification machine learning models more than once, for example, 10, 20, 30, 40, 50 or even more times.

In embodiments, the candidate model (combination of subset of model parameters and candidate classification machine learning model 130) generated by the classification engine 128 can be compared in performance to a model generated using the full set of clinical parameters of the training data 102. For example, the classification engine 128 can execute a classification machine learning model 122 using the full set of clinical parameters, in a similar manner as for executing the classification machine learning model 130 based on the subsets of model parameters, to represent a baseline for model performance. The candidate model can be compared to the model generated using the full set of clinical parameters using DCA. The machine learning engine 204 can execute an imputation algorithm to process clinical parameters with missing data.

Figure 2:
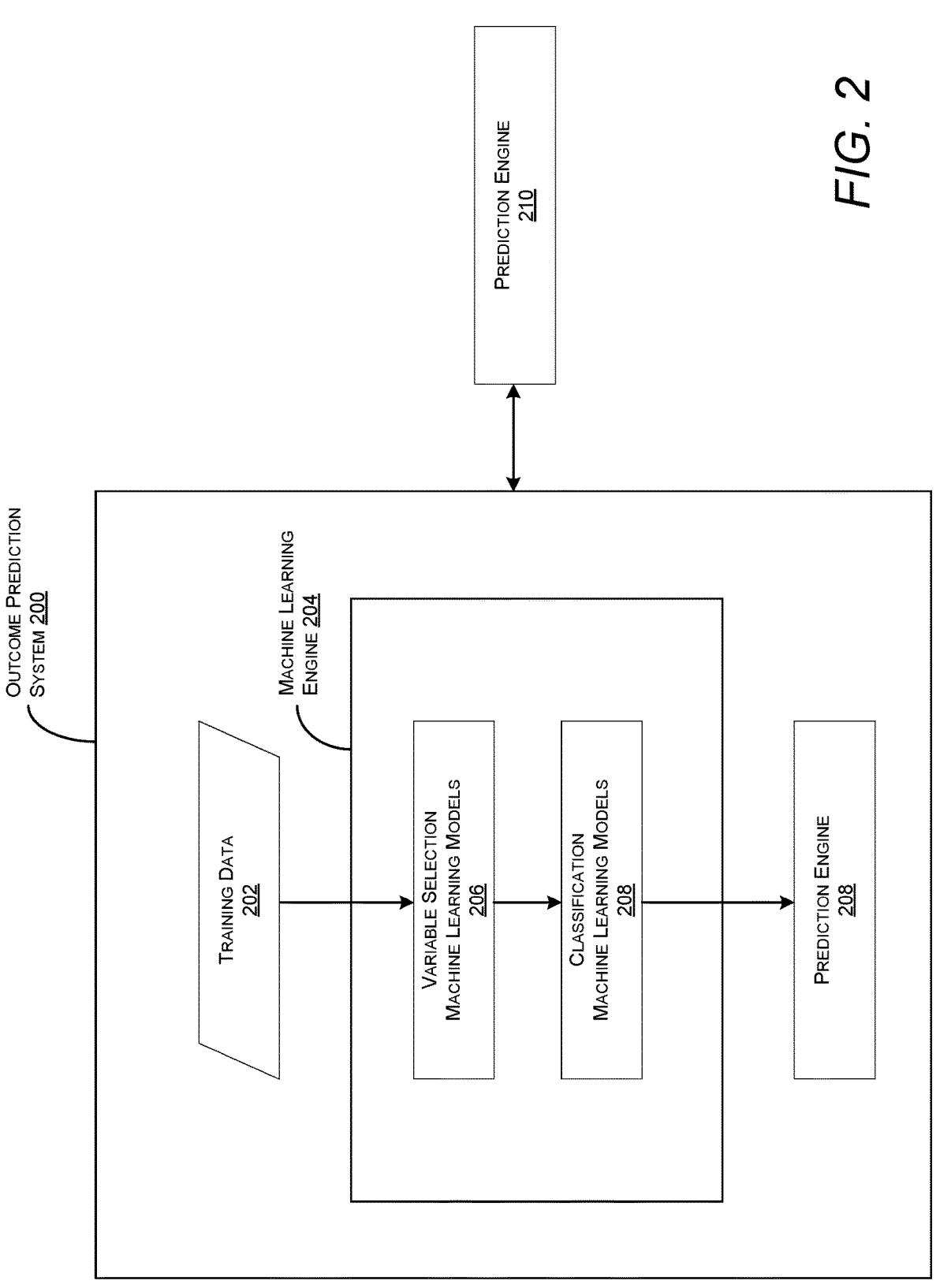
FIG. 2 illustrates a block diagram for an outcome prediction system for predicting one or more clinical outcomes for an individual as described herein.

Referring to FIG. 2, in embodiments, the Outcome Prediction System 200 includes a prediction engine 208. The prediction engine 208 can predict one or more clinical outcomes specific to at least one second subject. The prediction engine 208 can receive, for the at least one second subject, a second value of at least one clinical parameter of the plurality of clinical parameters.

In embodiments, at least one of the received second values corresponds to a model parameter of the subset of model parameters used in the candidate classification machine learning model 130. If the prediction engine 208 receives several second values of clinical parameters, of which at least one does not correspond to a model parameter of the subset of model parameters, the prediction engine 208 may execute an imputation algorithm to generate a value for such a missing parameter.

The prediction engine 208 can execute the candidate classification machine learning model 130 using the corresponding subset of model parameters and the second value of the at least one clinical parameter to calculate the pneumonia outcome specific to the at least one second subject. In an example, the candidate classification machine learning algorithm 130 may include a naïve Bayes model based on the following model parameters (and received the indicated second values for the second subject): IP-10 (500); IL-10 (35); MCP1 (3000); platelets administered to the second subject (2); summation of all blood products administered to the subject (35); red blood cells administered to the subject (25); AIS of the head (4); and AIS of the abdomen (5). Using these values, the prediction engine 130 can cause the candidate classification machine learning model 130 to calculate the probabilities that the second subject would have those values for the model parameters given that the subject has pneumonia: IP-10 (0.0007); IL-10 (0.01); MCP1 (0.0002); platelets administered to the second subject (0.16); summation of all blood products administered to the subject (0.01); red blood cells administered to the subject (0.03);

AIS of the head (0.13); and AIS of the abdomen (0.10), resulting in an overall probability of 8.736e−16. Similarly, the prediction engine 208 can determine an overall probability associated with the given not pneumonia case to be approximately zero. As such, the prediction engine 130 can output a prediction that the second subject has pneumonia based on the overall probabilities (e.g., based on a ratio of the overall probabilities).

As shown in FIG. 2, the outcome prediction system 200 includes the prediction engine 208. In embodiments, a remote device 530 may additionally or alternatively include a separate, but similar prediction engine 210. The prediction engine 210 can incorporate features of the prediction engine 208. The remote device 530 can incorporate features of the computing environment. The remote device 430 can communicate with the outcome prediction system 200 using any of a variety of wired or wireless communication protocols (including communicating via a network 528). For example, the remote device 530 can receive the prediction engine 208 (or the candidate classification machine learning model 230 with the corresponding subset of model parameters) from the outcome prediction system 200.

In various embodiments, the outcome prediction system 200 and/or the remote device 530 can receive the second values of the plurality of clinical parameters through a user interface, and can output the predictions of one or more clinical outcomes responsive to receiving the second values. The remote device 530 can be implemented as a client device executing the prediction engine 210 as a local application which receives the second values and transmits the second values to the outcome prediction system 200; the outcome prediction system 200 can be implemented as a server device which calculates the prediction of the one or more clinical outcomes specific to the second subject and transmits the calculated prediction to the prediction engine 210. The remote device 530 may then output the calculated prediction received from the outcome prediction system 200.

In embodiments, the outcome prediction system 200 can update the training data 202 based on the second values received for the second subjects, as well as the predicted pneumonia outcomes. As such, the outcome prediction system 200 can continually learn from new data regarding subjects. The outcome prediction system 200 can store the predicted pneumonia outcome with an association to the second value(s) received for the second subject in the training data 202. The predicted pneumonia outcome may be stored with an indication of being a predicted value (as compared to the known pneumonia outcomes for the plurality of first subjects), which can enable the machine learning engine 204 to process predicted outcome data stored in the training data 202 differently than known outcome data. In addition, it will be appreciated that over time, the second subject based on which a predicted outcome was generate may also have a known pneumonia outcome (e.g., based on the onset of symptoms indicating that the second subject has pneumonia, or based on an indication that the second subject does not have pneumonia, such as a sufficient period of time passing subsequent to the generation of the predicted pneumonia outcome). The outcome prediction system 200 can store the known pneumonia outcome with an association to the second value(s) received for the second subject. The outcome prediction system 200 can also store the known pneumonia outcome with an indication of an update relative to the predicted pneumonia outcome, which can enable the machine learning engine 204 to learn from the update and thus improve the variable selection and classification processes used to generate and select the candidate classification algorithm/subset of model parameters for use by the prediction engine 208. In embodiments, the outcome prediction system 200 calculates a difference between the predicted pneumonia outcome and the known pneumonia outcome, and stores this difference as the indication of the update.

Figure 3:
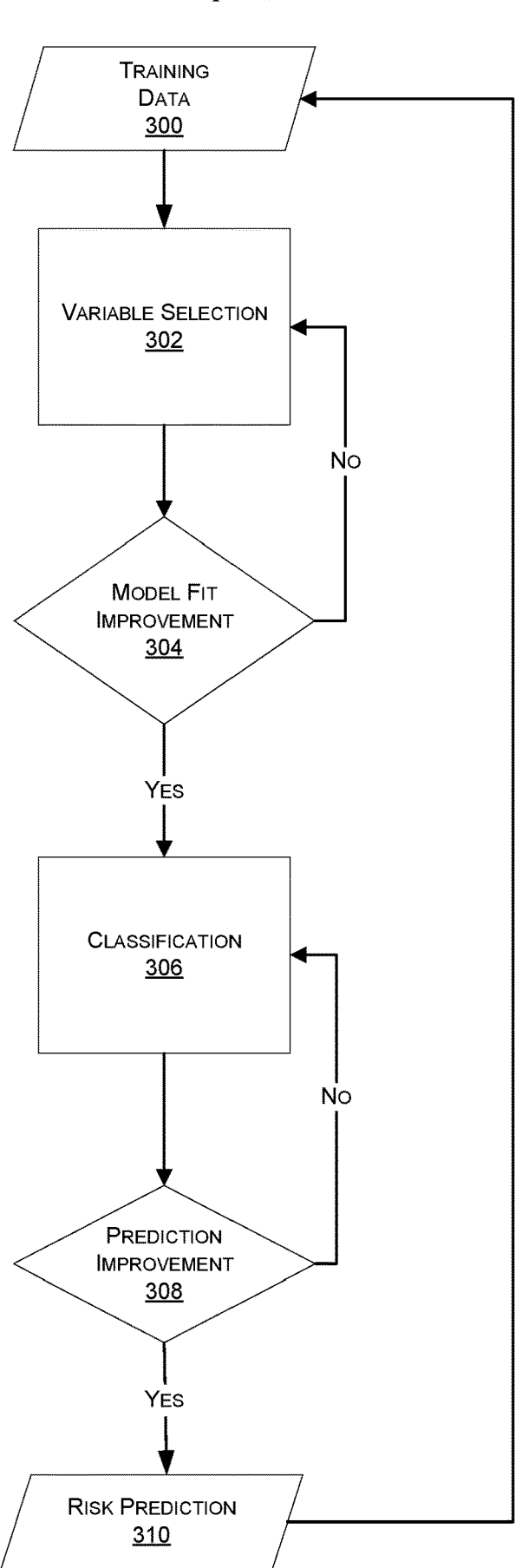
FIG. 3 illustrates a flow-chart for an outcome prediction system and the data flow and decision trees that are required at each stage of the system.

Referring now to FIG. 3, a process for predicting one or more clinical outcomes and flow of data that occurs in the machine learning engine 204. The process can be performed by various systems described herein, including the outcome prediction system 200 and or the remote device 530. The training data 302 comprises clinical parameters 104 (e.g., mechanism of injury data 106, biomarker data 108, index/score data 110, and diagnostic imaging data 112), clinical outcome data 114, and administrative health data 116.

In embodiments, preprocessing is executed on the training data. Pre-processing may be performed before variable selection 302 and/or classification 306 are performed on the data. In embodiments, an imputation algorithm can be executed to generate values for missing data in the training database 105. In embodiments, at least one of up-sampling or predictor rank transformations is executed on the data of the training database. Up-sampling and/or predictor rank transformation can be executed only for variable selection to accommodate class imbalance and non-normality in the data. While up-sampling or predictor rank transformations are discussed, many others are contemplated.

At variable selection 302, one or more variable selection machine learning models 122 are executed using the data stored in the training database to select, for each variable selection machine learning models. The subsets of model parameters are selected from the plurality of clinical parameters of the training data 300, such that a count of each subset of model parameters is less than a count of the clinical parameters. Variable selection machine learning engines such as constraint-based algorithms, constrain-based structure learning algorithms, and/or constraint-based local discovery learning algorithms can be used to select the subsets of model parameters. For example, the machine learning engine 204 can execute machine learning algorithms from the "bnlearn" R package, including but not limited to the Grow-Shrink ("gs"), Incremental Association Markov Blanket ("iamb"), Fast Incremental Association ("fast.iamb"), Max-Min Parents & Children ("mmpc"), or Semi-Interleaved Hiton-PC ("si.hiton.pc") algorithms. While these variable selection are enumerated, many others are contemplated. In embodiments, the clinical parameters are randomly re-ordered prior to variable selection.

At model fit improvement 304, the results of the variable selection machine learning models are compared in an iterative process; when a variable selection machine learning model is executed and tested, it is compared to the previous models, if the model improves model fit that model is selected as the best model, if the model does not improve model fit it is discarded and the next model is tested. This process repeats until the optimal model is discovered.

At classification 306, one or more classification machine learning models is executed using each subset of model parameters to generate predictions of one or more clinical outcomes based on the subsets of model parameters. The classification algorithms may be executed by identifying first values of clinical parameters in the training database corresponding to each subset of model parameters, and generating predictions of pneumonia outcomes using the identified first values. In embodiments, the classification algorithms include a plurality of linear discriminant analysis (lda), classification and regression trees (cart), k-nearest neighbors (knn), support vector machine (svm), logistic regression (glm), random forest (rf), generalized linear models (glmnet) and/or naïve Bayes (nb) algorithms. While these algorithms for the classification machine learning models are discussed, many more are contemplated.

At prediction improvement, 308 at least one performance metric is calculated for each classification machine learning model (e.g., each combination of (i) a subset of model parameters selected using a variable selection machine learning model and (ii) a classification machine learning model used to generate one or more clinical outcome predictions). The performance metrics can represent the ability of each combination to predict one or more clinical outcomes. The performance metric can include at least one of a Kappa score, a sensitivity, or a specificity. The Kappa score indicates a comparison of an observed accuracy of the combination of the subset of model parameters and the classification algorithm to an expected accuracy. In embodiments, an ROC curve can be generated based on the sensitivity and the specificity. An AUC can be calculated based on the ROC curve. In embodiments, the candidate classification machine learning model can be evaluated by further performance metrics. For example, the candidate classification machine learning model can be evaluated based on Accuracy, No Information Rate, positive predictive value and negative predictive value. While these performance metrics are discussed, many more are contemplated. Then, a candidate classification machine learning algorithm is selected based on the performance metric(s). Various policies, heuristics, or other rules can be applied based on the performance metric(s) to select a candidate classification algorithm (and corresponding subset of model parameters selected by one of the variable selection algorithms). For example, values for each performance metrics can be compared to respective threshold values, and a classification machine learning model can be determined to be a candidate classification machine learning model (or a potential candidate) responsive to the value for the performance metric exceeding the threshold. In embodiments, the candidate classification machine learning model and corresponding subset of model parameters are selected based on the rule: identify the combination having (1) a highest Kappa score; subsequently, (2) a highest sensitivity; and (3) subsequently, a specificity greater than a threshold specificity.

At risk prediction 310 second values of clinical parameters are received. The second values may be received for at least one second subject. In embodiments, at least one of the received second values corresponds to a model parameter of the subset of model parameters used in the candidate classification machine learning algorithm. If several second values of clinical parameters are received, of which at least one does not correspond to a model parameter of the subset of model parameters, an imputation algorithm may be executed to generate a value for such a missing parameter. The candidate classification machine learning is executed using the corresponding subset of model parameters and the second value of the at least one clinical parameter to calculate the prediction of the pneumonia outcome specific to the at least one second subject. The predicted one or more clinical outcomes specific to the at least one second subject is outputted. For example, the predicted one or more clinical outcomes may be displayed on an electronic device to a user or may be provided as an audio output. The predicted one or more clinical outcomes may be transmitted to another device. The predicted one or more clinical outcomes may include at least one of an indication that the second subject has one or more clinical outcomes, that the second subject is likely to have one or more clinical outcomes (e.g., relative to a confidence threshold), or that the second subject has an increased risk for one or more clinical outcomes relative to a reference risk level.

In embodiments, the methods described herein involve five major components: (1) initial data exploration, (2) variable and/or feature selection, (3) classification, (4) model selection, (5) deployment and self-improvement. It will be understood by those possessing ordinary skill in the art that these stages may not be discrete entities and there may be overlap between them, and that the output from each stage may be used to inform, calibrate, and/or improve other stages of the engine and the machine learning engine. To perform variable selection on an entire set of clinical parameters, constraint-based algorithms and constraint-based local discovery learning algorithms, such as from the "bnlearn" R package, can be used in a customized method to search the input dataset for nodes of Bayesian networks. Variable selection may be performed by removing variables that are highly correlated. In embodiments where subjects have an injury (such as an injury that puts them at risk for pneumonia, summations of wound volume and wound surface area can be added to the variable set to account for patient wound burden. One or more of up-sampling, data imputation, and predictor rank transformations can be performed to improve variable selection and accommodate class imbalance in the data. The variable sets can be run in sundry binary classification algorithms, and the best variable set and binary classification algorithm combination that firstly produces the highest Kappa and then the highest Sensitivity and reasonable Specificity can be chosen. Optionally, the resultant models can be examined using Accuracy, No Information Rate, positive predictive value and negative predictive value. Optionally, model performance can be further assessed using Receiver Operator Characteristic Curves (ROC), area under curve (AUC), and Decision Curve Analysis (DCA).

In embodiments, comparisons of the variable selected models to the full variable models shows better performance in the former. This is a strength of the methods described herein, since over-parameterization frequently leads to model underperformance. In variable selected models as described herein, the ROC curves and their respective AUCs show that the models have good predictive ability. Similarly, these models have higher Accuracy and Kappa statistics than the full variable models.

Figure 4:
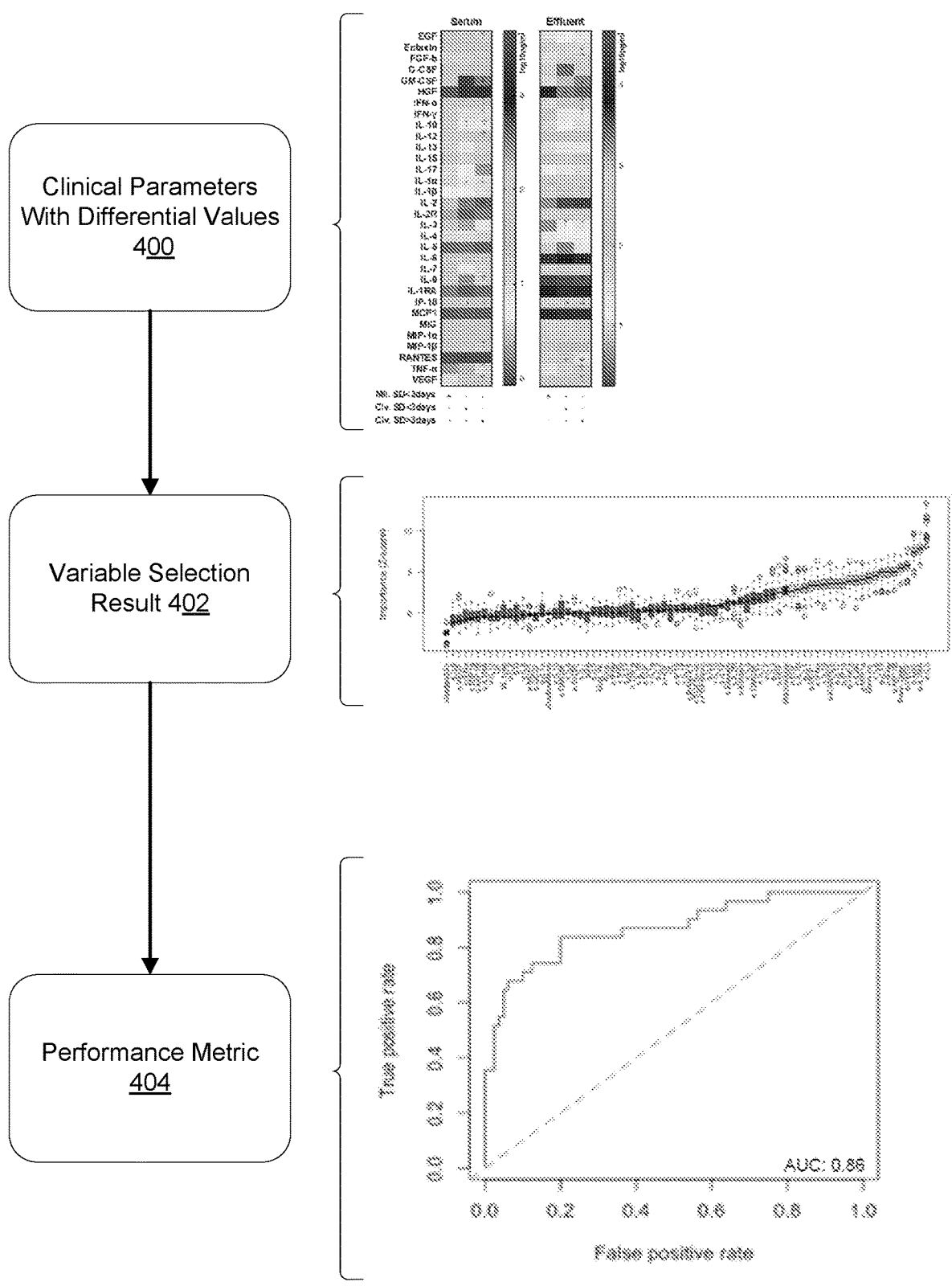
FIG. 4 illustrates an embodiment of differential levels of clinical parameters, results of a candidate variable selection machine learning algorithm, and a chart of performance metrics of a candidate classification machine learning model.

FIG. 4 illustrates an example of clinical parameters with differential values 400 that drive the variable selection, a variable selection result 402 that depicts the importance of each variable on the fit and prediction capacity of the model, and a performance metric 404 that evaluates the accuracy, sensitivity, and specificity of classification. Clinical parameters with differential values 400 from an analysis of clinical parameters obtained in a study of wound closure are shown. The variable selection result 402 from a Boruta algorithm and the receiver operating characteristic curve performance metric 404 from classification via random forest for prediction of a delayed wound closure outcome are shown.

In embodiments, the methods disclosed herein relate to determining a subject's risk profile for one or more clinical outcomes, determining if a subject has an increased risk of developing one or more clinical outcomes, assessing risk factors in a subject, detecting levels of biomarkers, and treating a subject for one or more clinical outcomes. In accordance with any embodiments of the methods described herein, the subject may be assessed prior to the detection of symptoms of one or more clinical outcomes, such as prior to detection of symptoms of one or more clinical outcomes. In accordance with any embodiments of the methods described herein, the test subject may be assessed prior to the onset of any detectable symptoms of one or more clinical outcomes, such as prior to the subject having symptoms of one or more clinical outcomes detectable by one or more such methodologies. In accordance with any embodiments of the methods described herein, the test subject may have an injury, condition, or wound that puts the subject at risk of developing one or more clinical outcomes, such as a blast injury, a crush injury, a gunshot wound, or an extremity wound.

In embodiments, there are provided methods of assessing risk factors (e.g., clinical parameters) in a subject, the methods comprising, consisting of, or consisting essentially of measuring, assessing, detecting, assaying, and/or determining one or more clinical parameters, such as one or more selected from level of epidermal growth factor (EGF) in a sample from the subject, level of eotaxin-1 (CCL11) in a sample from the subject, level of basic fibroblast growth factor (bFGF) in a sample from the subject, level of granulocyte colony-stimulating factor (G-CSF) in a sample from the subject, level of granulocyte-macrophage colony-stimulating factor (GM-CSF) in a sample from the subject, level of hepatocyte growth factor (HGF) in a sample from the subject, level of interferon alpha (IFN-$\alpha$) in a sample from the subject, level of interferon gamma (IFN-$\gamma$) in a sample from the subject, level of interleukin 10 (IL-10) in a sample from the subject, level of interleukin 12 (IL-12) in a sample from the subject, level of interleukin 13 (IL-13) in a sample from the subject, level of interleukin 15 (IL-15) in a sample from the subject, level of interleukin 17 (IL-17) in a sample from the subject, level of interleukin 1 alpha (IL-1$\alpha$) in a sample from the subject, level of interleukin 1 beta (IL-I$\beta$) in a sample from the subject, level of interleukin 1 receptor antagonist (IL-1RA) in a sample from the subject, level of interleukin 2 (IL-2) in a sample from the subject, level of interleukin 2 receptor (IL-2R) in a sample from the subject, level of interleukin 3 (IL-3) in a sample from the subject, level of interleukin 4 (IL-4) in a sample from the subject, level of interleukin 5 (IL-5) in a sample from the subject, level of interleukin 6 (IL-6) in a sample from the subject, level of interleukin 7 (IL-7) in a sample from the subject, level of interleukin 8 (IL-8) in a sample from the subject, level of interferon gamma induced protein 10 (IP-10) in a sample from the subject, level of monocyte chemoattractant protein 1 (MCP-1) in a sample from the subject, level of monokine induced by gamma interferon (MIG) in a sample from the subject, level of macrophage inflammatory protein 1 alpha (MIP-1$\alpha$) in a sample from the subject, level of macrophage inflammatory protein 1 alpha (MIP-1$\beta$) in a sample from the subject, level of chemokine (C-C motif) ligand 5 (CCL5) in a sample from the subject, level of tumor necrosis factor alpha (TNF$\alpha$) in a sample from the subject, level of vascular endothelial growth factor (VEGF) in a sample from the subject, amount of whole blood cells administered to the subject, amount of red blood cells (RBCs) administered to the subject, amount of packed red blood cells (PRBCs) administered to the subject, amount of platelets administered to the subject, summation of all blood products administered to the subject, level of total packed RBCs, Injury Severity Score (ISS), Abbreviated injury scale (AIS) of abdomen, AIS of chest (thorax), AIS of extremity, AIS of face, AIS of head, and AIS of skin. In particular embodiments, there are provided methods of assessing risk factors (e.g., clinical parameters) in a subject, the methods comprising, consisting of, or consisting essentially of measuring, assessing, detecting, assaying, and/or determining one or more clinical parameters, such as one or more selected from AIS of head in the subject, AIS of abdomen in the subject, amount of platelets administered to the subject, level of total packed RBCs administered to the subject, summation of all blood products administered to the subject, level of IP-10 in a serum sample from the subject, level of IL-10 in a serum sample from the subject, and level of MCP-1 in a serum sample from the subject.

In embodiments, there are provided methods of detecting levels of biomarkers, the methods comprising, consisting of, or consisting essentially of measuring, detecting, assaying, or determining in one or more samples from the subject levels of one or more biomarkers selected from level of epidermal growth factor (EGF) in a sample from the subject, level of eotaxin-1 (CCL11) in a sample from the subject, level of basic fibroblast growth factor (bFGF) in a sample from the subject, level of granulocyte colony-stimulating factor (G-CSF) in a sample from the subject, level of granulocyte-macrophage colony-stimulating factor (GM-CSF) in a sample from the subject, level of hepatocyte growth factor (HGF) in a sample from the subject, level of interferon alpha (IFN-α) in a sample from the subject, level of interferon gamma (IFN-γ) in a sample from the subject, level of interleukin 10 (IL-10) in a sample from the subject, level of interleukin 12 (IL-12) in a sample from the subject, level of interleukin 13 (IL-13) in a sample from the subject, level of interleukin 15 (IL-15) in a sample from the subject, level of interleukin 17 (IL-17) in a sample from the subject, level of interleukin 1 alpha (IL-1α) in a sample from the subject, level of interleukin 1 beta (IL-113) in a sample from the subject, level of interleukin 1 receptor antagonist (IL-1RA) in a sample from the subject, level of interleukin 2 (IL-2) in a sample from the subject, level of interleukin 2 receptor (IL-2R) in a sample from the subject, level of interleukin 3 (IL-3) in a sample from the subject, level of interleukin 4 (IL-4) in a sample from the subject, level of interleukin 5 (IL-5) in a sample from the subject, level of interleukin 6 (IL-6) in a sample from the subject, level of interleukin 7 (IL-7) in a sample from the subject, level of interleukin 8 (IL-8) in a sample from the subject, level of interferon gamma induced protein 10 (IP-10) in a sample from the subject, level of monocyte chemoattractant protein 1 (MCP-1) in a sample from the subject, level of monokine induced by gamma interferon (MIG) in a sample from the subject, level of macrophage inflammatory protein 1 alpha (MIP-1α) in a sample from the subject, level of macrophage inflammatory protein 1 alpha (MIP-1β) in a sample from the subject, level of chemokine (C-C motif) ligand 5 (CCL5) in a sample from the subject, level of tumor necrosis factor alpha (TNF-α) in a sample from the subject, level of vascular endothelial growth factor (VEGF) in a sample from the subject.

In particular embodiments, there are provided methods of detecting levels of biomarkers, the methods comprising, consisting of, or consisting essentially of measuring, detecting, assaying, or determining in one or more samples from the subject levels of one or more biomarkers selected from IP-10, IL-10 and MCP-1. In embodiments, the one or more biomarkers comprise, consist of, or consist essentially of levels of IP-10, IL-10 and MCP-1.

In embodiments, one or more clinical parameters, two or more clinical parameters, three or more clinical parameters, four or more clinical parameters, five or more clinical parameters, six or more clinical parameters, seven or more clinical parameters, eight or more clinical parameters, nine or more clinical parameters, ten or more clinical parameters, 11 or more clinical parameters, 12 or more clinical parameters, 13 or more clinical parameters, 14 or more clinical parameters, 15 or more clinical parameters, 16 or more clinical parameters, 17 or more clinical parameters, 18 or more clinical parameters, 19 or more clinical parameters, 20 or more clinical parameters, 21 or more clinical parameters, 22 or more clinical parameters, 23 or more clinical parameters, 24 or more clinical parameters, 25 or more clinical parameters, 26 or more clinical parameters, 27 or more clinical parameters, 28 or more clinical parameters, 29 or more clinical parameters, 30 or more clinical parameters, 31 or more clinical parameters, 32 or more clinical parameters, 33 or more clinical parameters, 34 or more clinical parameters, 35 or more clinical parameters, 36 or more clinical parameters, 37 or more clinical parameters, 38 or more clinical parameters, 39 or more clinical parameters, 40 or more clinical parameters, 41 or more clinical parameters, 42 or more clinical parameters, 43 or more clinical parameters, 44 or more clinical parameters, 45 or more clinical parameters, such as selected from those set forth above are measured, assessed, detected, assayed, and/or determined. In particular embodiments, 2, 3, 4, 5, 6, 7, or 8 clinical parameters are measured, assessed, detected, assayed, and/or determined.

To assay, detect, measure, and/or determine levels of individual clinical parameters, one or more samples is taken or isolated from the subject. In embodiments, at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 samples are taken or isolated from the subject. The one or more samples may or may not be processed prior assaying levels of the factors, risk factors, biomarkers, clinical parameters, and/or components. For example, whole blood may be taken from an individual and the blood sample may be processed, e.g., centrifuged, to isolate plasma or serum from the blood. The one or more samples may or may not be stored, e.g., frozen, prior to processing or analysis. In embodiments, one or more clinical parameters selected from are detected in a sample from a subject that is not a serum sample, such as wound effluent.

In embodiments, levels of individual biomarkers in a sample isolated from a subject are assessed, detected, measured, and/or determined using mass spectrometry in conjunction with ultra-performance liquid chromatography (UPLC), high-performance liquid chromatography (HPLC), gas chromatography (GC), gas chromatography/mass spectroscopy (GC/MS), or UPLC. Other methods of assessing biomarkers include biological methods, such as but not limited to ELISA assays, Western Blot, and multiplexed immunoassays. Other techniques may include using quantitative arrays, PCR, RNA sequencing, DNA sequencing, and Northern Blot analysis. Other techniques include Luminex proteomic data, RNAseq, transcriptomic data, quantitative polymerase chain reaction (qPCR) data, microarray, and quantitative bacteriology data.

In embodiments, the biomarkers include proteins and nucleic acids isolated from biological samples, for example tissue, organ, or biological fluids of a subject. Examples of biological fluids include blood, serum, plasma, sweat, urine, saliva, peritoneal fluid, wound effluent, and spinal fluid.

The present disclosure also describes microarrays including biomarkers comprising proteins or nucleic acid for predicting one or more clinical outcomes. In embodiments, proteins and nucleic acids can be linked to chips, such as microarray chips (see U.S. Pat. Nos. 6,040,138 and 7,148, 058). Binding to proteins or nucleic acids on microarrays can be detected by scanning the microarray with a variety of laser or charge coupled device (CCD)-based scanners, and extracting features with software packages, for example, Imagene (Biodiscovery, Hawthorne, CA), Feature Extraction Software (Agilent), Scanalyze (Eisen, M. 1999. SCANALYZE User Manual; Stanford Univ., Stanford, Calif. Ver 2.32.), or GenePix (Axon Instruments). A microarray panel including one or more biomarkers for a clinical outcome can be used for predicting the risk of a subject in developing a clinical outcome and/or for monitoring subject undergoing treatment for a clinical outcome.

To determine levels of clinical parameters, particularly biomarkers, it is not necessary that an entire biomarker molecule, e.g., a full length protein or an entire RNA transcript, be present or fully sequenced. In other words, determining levels of, for example, a fragment of protein being analyzed may be sufficient to conclude or assess that an individual component of the risk profile being analyzed is increased or decreased. Similarly, if, for example, arrays or blots are used to determine biomarker levels, the presence, absence, and/or strength of a detectable signal may be sufficient to assess levels of biomarkers.

Biomarkers can be detected, assayed, or measured using the Luminex™ immune assay platform, available from ThermoFisher Scientific. For example the Cytokine & Chemokine 34-Plex Human ProcartaPlex™ Panel 1A (cat #EPX340-12167-901) detects the following targets in a single serum or plasma sample: Eotaxin/CCL11; GM-CSF; GRO alpha/CXCL1; IFN alpha; IFN gamma; IL-1 beta; IL-1 alpha; IL-1RA; IL-2; IL-4; IL-5; IL-6; IL-7; IL-8/CXCL8; IL-9; IL-10; IL-12 p70; IL-13; IL-15; IL-17A; IL-18; IL-21; IL-22; IL-23; IL-27; IL-31; IP-10/CXCL10; MCP-1/CCL2; MIP-1 alpha/CCL3; MIP-1 beta/CCL4; RANTES/CCL5; SDF1 alpha/CXCL12; TNF alpha; TNF beta/LTA. While this set of markers and this platform is discussed, it is known to persons having ordinary skill in the art that additional markers may be measured using similar types of platforms (e.g., other multiplex assays).

In embodiments, clinical parameters are detected, measured, assayed, assessed, and/or determined in a sample isolated from the subject at different time points, such as before, at a first time point after, and/or at a subsequent time point after the subject contracts an injury, condition, or wound that puts the subject at risk of developing pneumonia, such as a blast injury, a crush injury, a gunshot wound, or an extremity wound. For example, embodiments of the methods described herein may comprise detecting biomarkers at two, three, four, five, six, seven, eight, nine, 10 or even more time points over a period of time, such as a week or more, two weeks or more, three weeks or more, four weeks or more, a month or more, two months or more, three months or more, four months or more, five months or more, six months or more, seven months or more, eight months or more, nine months or more, ten months or more, 11 months or more, a year or more or even two years or longer. The methods also include embodiments in which the subject is assessed before and/or during and/or after treatment for pneumonia. In embodiments, the methods are useful for monitoring the efficacy of treatment of pneumonia, and comprise detecting clinical parameters, such as biomarkers in a sample isolated from the subject, at least one, two, three, four, five, six, seven, eight, nine or 10 or more different time points prior to beginning treatment for pneumonia and subsequently detecting clinical parameters, such as at least one, two, three, four, five, six, seven, eight, nine or 10 or more different time points after beginning of treatment for pneumonia, and determining the changes, if any, in the levels detected. The treatment may be any treatment designed to cure, remove or diminish the symptoms and/or cause(s) of pneumonia.

In embodiments, there are provided methods of detecting clinical parameters in a subject, the method comprising, consisting of, or consisting essentially of measuring levels of one or more clinical parameters selected from abdominal injury, head injury, platelets and PRBCs received, total PRBCs, and serum levels of interferon gamma induced protein 10 (IP-10), monocyte chemoattractant protein 1 (MCP-1), and interleukin 10 (IL-10). In embodiments, the methods comprise detecting elevated levels. As used herein, "elevated" refers to a level or value that is increased relative to a reference level or value. As used herein, "reduced" refers to a level or value that is reduced relative to a reference level or value. In embodiments, the reference value is a value previously detected, measured, assayed, assessed, or determined for the subject. In other embodiments, the reference value is detected, measured, assayed, assessed, or determined for a population of one or more reference subjects at a time when the reference subjects did not have detectable symptoms of one or more clinical outcomes.

In embodiments, there are provided methods of determining a risk profile for one or more clinical outcomes, wherein the clinical outcomes include one or more of acute kidney injury, acute respiratory distress, bacteremia, heterotopic ossification, pneumonia, post-traumatic sterile inflammation, sepsis, wound closure, or vasospasm and/or mortality following traumatic brain injury, and wherein the risk profile comprises, consists of, or consists essentially of one or more components based on one or more clinical parameters selected from level of epidermal growth factor (EGF) in a sample from the subject, level of eotaxin-1 (CCL11) in a sample from the subject, level of basic fibroblast growth factor (bFGF) in a sample from the subject, level of granulocyte colony-stimulating factor (G-CSF) in a sample from the subject, level of granulocyte-macrophage colony-stimulating factor (GM-CSF) in a sample from the subject, level of hepatocyte growth factor (HGF) in a sample from the subject, level of interferon alpha (IFN-$\alpha$) in a sample from the subject, level of interferon gamma (IFN-$\gamma$) in a sample from the subject, level of interleukin 10 (IL-10) in a sample from the subject, level of interleukin 12 (IL-12) in a sample from the subject, level of interleukin 13 (IL-13) in a sample from the subject, level of interleukin 15 (IL-15) in a sample from the subject, level of interleukin 17 (IL-17) in a sample from the subject, level of interleukin 1 alpha (IL-1$\alpha$) in a sample from the subject, level of interleukin 1 beta (IL-I$\beta$) in a sample from the subject, level of interleukin 1 receptor antagonist (IL-1RA) in a sample from the subject, level of interleukin 2 (IL-2) in a sample from the subject, level of interleukin 2 receptor (IL-2R) in a sample from the subject, level of interleukin 3 (IL-3) in a sample from the subject, level of interleukin 4 (IL-4) in a sample from the subject, level of interleukin 5 (IL-5) in a sample from the subject, level of interleukin 6 (IL-6) in a sample from the subject, level of interleukin 7 (IL-7) in a sample from the subject, level of interleukin 8 (IL-8) in a sample from the subject, level of interferon gamma induced protein 10 (IP-10) in a sample from the subject, level of monocyte chemoattractant protein 1 (MCP-1) in a sample from the subject, level of monokine induced by gamma interferon (MIG) in a sample from the subject, level of macrophage inflammatory protein 1 alpha (MIP-1$\alpha$) in a sample from the subject, level of macrophage inflammatory protein 1 alpha (MIP-1$\beta$) in a sample from the subject, level of chemokine (C-C motif)

ligand 5 (CCL5) in a sample from the subject, level of tumor necrosis factor alpha (TNF-α) in a sample from the subject, level of vascular endothelial growth factor (VEGF) in a sample from the subject, amount of whole blood cells administered to the subject, amount of red blood cells (RBCs) administered to the subject, amount of packed red blood cells (PRBCs) administered to the subject, amount of platelets administered to the subject, summation of all blood products administered to the subject, level of total packed RBCs, Injury Severity Score (ISS), Abbreviated injury scale (AIS) of abdomen, AIS of chest (thorax), AIS of extremity, AIS of face, AIS of head, and AIS of skin. Such methods may comprise, consist of or consist essentially of detecting the one or more clinical parameters for the subject, and calculating the subject's risk profile value from the detected clinical parameters.

In embodiments, the risk profile is calculated from one or more clinical parameters, two or more clinical parameters, three or more clinical parameters, four or more clinical parameters, five or more clinical parameters, six or more clinical parameters, seven or more clinical parameters, eight or more clinical parameters, nine or more clinical parameters, ten or more clinical parameters, 11 or more clinical parameters, 12 or more clinical parameters, 13 or more clinical parameters, 14 or more clinical parameters, 15 or more clinical parameters, 16 or more clinical parameters, 17 or more clinical parameters, 18 or more clinical parameters, 19 or more clinical parameters, 20 or more clinical parameters, 21 or more clinical parameters, 22 or more clinical parameters, 23 or more clinical parameters, 24 or more clinical parameters, 25 or more clinical parameters, 26 or more clinical parameters, 27 or more clinical parameters, 28 or more clinical parameters, 29 or more clinical parameters, 30 or more clinical parameters, 31 or more clinical parameters, 32 or more clinical parameters, 33 or more clinical parameters, 34 or more clinical parameters, 35 or more clinical parameters, 36 or more clinical parameters, 37 or more clinical parameters, 38 or more clinical parameters, 39 or more clinical parameters, 40 or more clinical parameters, 41 or more clinical parameters, 42 or more clinical parameters, 43 or more clinical parameters, 44 or more clinical parameters, 45 or more clinical parameters, such as selected from those set forth above. In particular embodiments, the risk profile is calculated from 2, 3, 4, 5, 6, 7, or 8 clinical parameters such as selected from those set forth above. In embodiments, a subject is diagnosed as having an increased risk of suffering from pneumonia if the subject's five, four, three, two or even one of the components or factors herein are at abnormal levels. It should be understood that individual levels of risk factor need not be correlated with increased risk in order for the risk profile value to indicate that the subject has an increased risk of developing pneumonia. In embodiments, one or more clinical parameters selected from the panel of biomarkers listed above are detected in a sample from a subject that is not a serum sample, such as wound effluent, or other biological fluids.

In embodiments, one or more clinical parameters are detected in a sample from the subject that is a biological fluid or tissue isolated from the subject. Biological fluids or tissues include but are not limited to whole blood, peripheral blood, serum, plasma, cerebrospinal fluid, wound effluent, urine, amniotic fluid, peritoneal fluid, lymph fluids, various external secretions of the respiratory, intestinal, and genito-urinary tracts, tears, saliva, white blood cells, solid tumors, lymphomas, leukemias, and myelomas. In embodiments, one or more clinical parameters are detected in a sample from the subject selected from a serum sample and wound effluent. In embodiments, the sample is a plasma sample from the subject.

In embodiments, the measurements of the individual components themselves are used in the risk profile, and these levels can be used to provide a "binary" value to each component, e.g., "elevated" or "not elevated." Each of the binary values can be converted to a number, e.g., "1" or "0," respectively.

In embodiments, the "risk profile value" can be a single value, number, factor or score given as an overall collective value to the individual components of the profile. For example, if each component is assigned a value, such as above, the component value may simply be the overall score of each individual or categorical value. For example, if four components of the risk profile for predicting one or more clinical outcomes are used and three of those components are assigned values of "+2" and one is assigned values of "+1," the risk profile in this example would be +7, with a normal value being, for example, "0." In this manner, the risk profile value could be a useful single number or score, the actual value or magnitude of which could be an indication of the actual risk of developing one or more clinical outcomes, e.g., the "more positive" the value, the greater the risk of developing one or more clinical outcomes.

In embodiments, the "risk profile value" can be a series of values, numbers, factors or scores given to the individual components of the overall profile. In another embodiment, the "risk profile value" may be a combination of values, numbers, factors or scores given to individual components of the profile as well as values, numbers, factors or scores collectively given to a group of components, such as a plasma marker portion. In another example, the risk profile value may comprise or consist of individual values, number or scores for specific component as well as values, numbers or scores for a group of components.

In embodiments, individual values from the risk profile can be used to develop a single score, such as a "combined risk index," which may utilize weighted scores from the individual component values reduced to a diagnostic number value. The combined risk index may also be generated using non-weighted scores from the individual component values. In such embodiments, when the "combined risk index" exceeds a specific threshold level, such as may be determined by a range of values developed similarly from a population of one or more control (normal) subjects, the individual may be deemed to have a high risk, or higher than normal risk, of developing one or more clinical outcomes, whereas maintaining a normal range value of the "combined risk index" would indicate a low or minimal risk of developing pneumonia. In these embodiments, the threshold value may be set by the combined risk index from a population of one or more control (normal) subjects.

In embodiments, the value of the risk profile can be the collection of data from the individual measurements, and need not be converted to a scoring system, such that the "risk profile value" is a collection of the individual measurements of the individual components of the profile.

In embodiments, the subject's risk profile is compared to a reference risk profile. In embodiments, the reference risk profile value is calculated from clinical parameters previously detected for the subject. Thus, the present application also includes methods of monitoring the progression of pneumonia in a subject, with the methods comprising determining the subject's risk profile at more than one time point. For example, embodiments of the methods of the present application will comprise determining the subject's risk profile at two, three, four, five, six, seven, eight, nine, 10 or even more time points over a period of time, such as a week or more, two weeks or more, three weeks or more, four weeks or more, a month or more, two months or more, three months or more, four months or more, five months or more, six months or more, seven months or more, eight months or more, nine months or more, ten months or more, 11 months or more, a year or more or even two years or longer. The methods described herein also include embodiments in which the subject's risk profile is assessed before and/or during and/or after treatment of one or more clinical outcomes. In other words, the present application also includes methods of monitoring the efficacy of treatment of one or more clinical outcomes by assessing the subject's risk profile over the course of the treatment and after the treatment. In embodiments, the methods of monitoring the efficacy of treatment of one or more clinical outcomes comprise determining the subject's risk profile at least one, two, three, four, five, six, seven, eight, nine or 10 or more different time points prior to the receipt of treatment for pneumonia and subsequently determining the subject's risk profile at least one, two, three, four, five, six, seven, eight, nine or 10 or more different time points after beginning of treatment for one or more clinical outcomes, and determining the changes, if any, in the risk profile of the subject. The treatment may be any treatment designed to cure, remove or diminish the symptoms and/or cause(s) of one or more clinical outcomes.

In other embodiments, the reference risk profile value is calculated from clinical parameters detected for a population of one or more reference subjects when the reference subjects did not have detectable symptoms of one or more clinical outcomes. In embodiments, the reference risk profile value is calculated from clinical parameters detected for a population of reference subjects having an injury, condition, or wound that puts the subject at risk of developing pneumonia, such as a blast injury, a crush injury, a gunshot wound, or an extremity wound.

The levels or values of the clinical parameters compared to reference levels can vary. In embodiments, the levels or values of any one or more of the factors, risk factors, biomarkers, clinical parameters, and/or components is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 30, 40, 50, 60, 70, 80, 90, 100, 500, 1,000, or 10,000 fold higher than reference levels or values. In embodiments, the levels or values of any one or more of the factors, risk factors, biomarkers, clinical parameters, and/or components is at least 1.05, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 30, 40, 50, 60, 70, 80, 90, 100, 500, 1,000, or 10,000 fold lower than reference levels or values. In the alternative, the levels or values of the factors or components may be normalized to a standard and these normalized levels or values can then be compared to one another to determine if a factor or component is lower, higher or about the same.

In embodiments, an increase in the subject's risk profile value as compared to a reference risk profile value indicates that the subject has an increased risk of developing one or more clinical outcomes.

In other embodiments, the subject's risk profile is compared to the profile that is deemed to be a "normal" risk profile. To establish a "normal" risk profile, an individual or group of individuals may be first assessed to ensure they have no signs, symptoms or diagnostic indicators that they may have one or more clinical outcomes. Then, the risk profile of the individual or group of individuals can then be determined to establish a "normal risk profile." In one embodiment, a normal risk profile can be ascertained from the same subject when the subject is deemed healthy, such as when the subject does not have an injury, condition, or wound that puts the subject at risk of developing one or more clinical outcomes, such as a blast injury, a crush injury, a gunshot wound, or an extremity wound and/or has no signs, symptoms or diagnostic indicators of pneumonia. In embodiments, however, a risk profile from a "normal subject," e.g., a "normal risk profile," is from a subject who has an injury or wound but has no signs, symptoms or diagnostic indicators that they may have one or more clinical outcomes, such as a subject who has a chest wound, but has no signs, symptoms or diagnostic indicators of one or more clinical outcomes, or a head wound but no signs, symptoms or diagnostic indicators of pneumonia, or has at least one wound in an extremity (arm, hand, finger(s), leg, foot, toe(s)), but no signs, symptoms or diagnostic indicators of one or more clinical outcomes. Thus, in embodiments, a "normal" risk profile is assessed in the same subject from whom the sample is taken, prior to the onset of any signs, symptoms or diagnostic indicators that they have one or more clinical outcomes. For example, the normal risk profile may be assessed in a longitudinal manner based on data regarding the subject at an earlier point in time, enabling a comparison between the risk profile (and values thereof) over time.

In another embodiment, a normal risk profile is assessed in a sample from a different subject or patient (from the subject being analyzed) and this different subject does not have or is not suspected of having one or more clinical outcomes. In still another embodiment, the normal risk profile is assessed in a population of healthy individuals, the constituents of which display no signs, symptoms or diagnostic indicators that they may have one or more clinical outcomes. Thus, the subject's risk profile can be compared to a normal risk profile generated from a single normal sample or a risk profile generated from more than one normal sample.

In embodiments, such as for univariate analysis, a Wilcoxon rank-sum test can be used to identify which biomarkers from specific patient groups are associated with a specific indication. The assessment of the levels of the individual components of the risk profile can be expressed as absolute or relative values and may or may not be expressed in relation to another component, a standard, an internal standard or another molecule or compound known to be in the sample. If the levels are assessed as relative to a standard or internal standard, the standard or internal standard may be added to the test sample prior to, during or after sample processing.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "engine," "module," or "system." Furthermore, aspects of the present disclosure may take the form of a computer program product embodied in one or more computer readable medium(s) having computer readable program code embodied thereon. Aspects of the present disclosure may be implemented using one or more analog and/or digital electrical or electronic components, and may include a microprocessor, a microcontroller, an application-specific integrated circuit (ASIC), a field programmable gate array (FPGA), programmable logic and/or other analog and/or digital circuit elements configured to perform various input/output, control, analysis and other functions described herein, such as by executing instructions of a computer program product.

Figure 5:
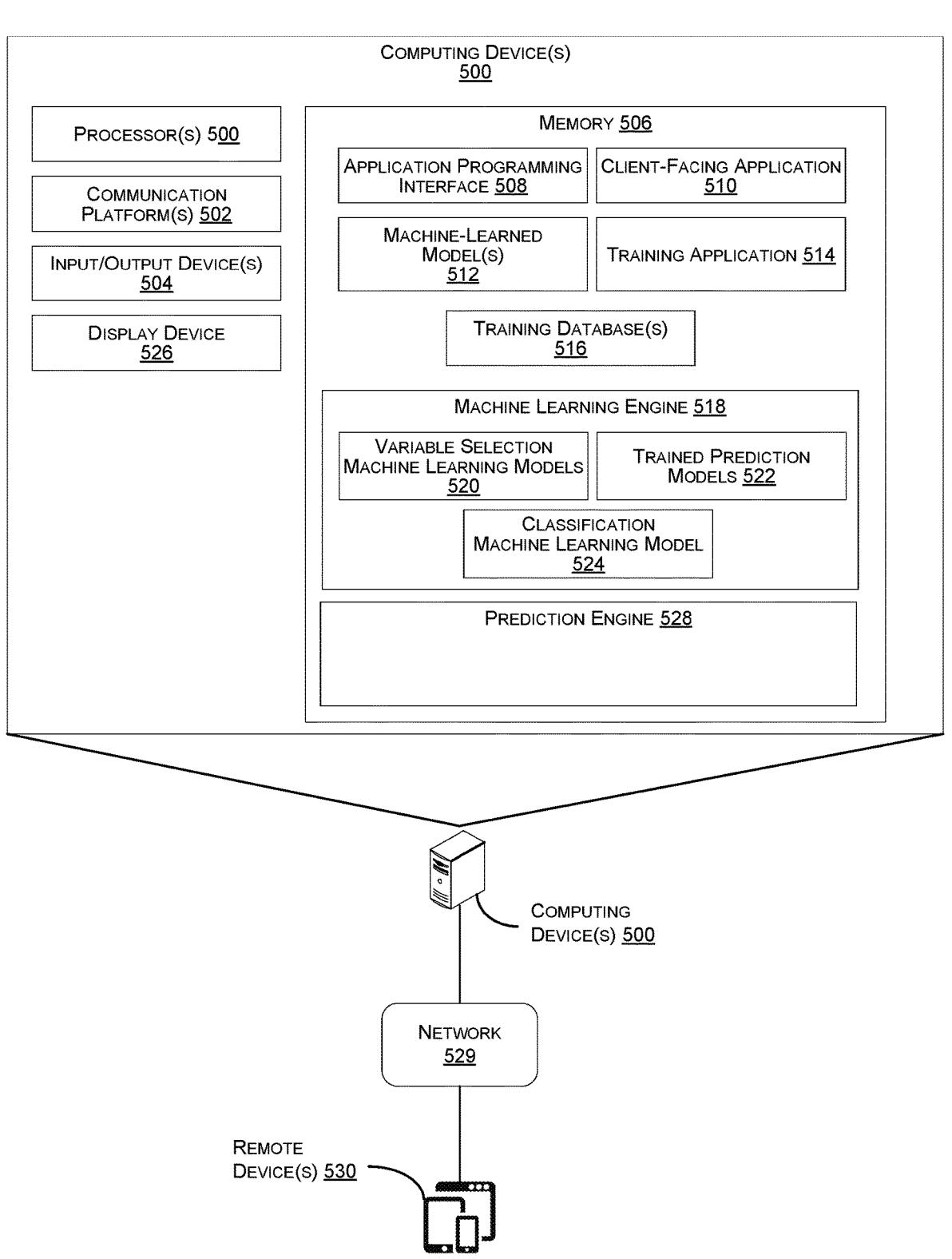
FIG. 5 illustrates an embodiment of a computational environment that involves a computing device, a network, and a remote device.

In embodiments, the computer device, computer readable media, network, and remote device may be arranged in the architecture depicted in FIG. 5. The computing device 500 houses at least, but is not limited to a processor(s) 500, communication platform(s) 502, input/output device(s) 504, memory 506, a machine learning engine 518, and a prediction engine 518. The memory includes at least, but is not limited to an application programming interface 508, a client-facing application 510, machine learned models 512, training application 514, and a training database 516, a machine learning engine 518 that comprises variable selection machine learning models 520, classification machine learning models 524, trained prediction models 522, and a display device 526. The memory also includes a prediction engine 528.

In embodiments, the computer devices is tethered to a remote device 530 through a network 529. The network enables communication via internet with a secure and protected host website operating the model algorithm and providing an output after predictive variables are entered.

In embodiments, the communication platform 502 can include communication electronics, wherein the communications electronics can be configured to transmit and receive electronic signals from a remote source, such as another electronic device, a cloud server, or an Internet resource. The communications electronics 120 can be configured to communicate using any number or combination of communication standards (e.g., Bluetooth, GSM, CDMA, TDNM, WCDMA, OFDM, GPRS, EV-DO, WiFi, WiMAX, S02.xx, UWB, LTE, satellite, etc). The communications electronics may also include wired communications features, such as USB ports, serial ports, IEEE 1394 ports, optical ports, parallel ports, and/or any other suitable wired communication port.

In embodiments, the input/output device(s) 504 may include one or more of a computer, a keyboard, a mouse, a mobile device (e.g., a mobile phone, an tables, a laptop), a screen, a microphone, or a printing device. The user input device can include various user interface elements such as keys, buttons, sliders, knobs, touchpads (e.g., resistive or capacitive touchpads), or microphones. In embodiments, the user interface device includes a touchscreen display device and user input device, such that the user interface device can receive user inputs as touch inputs and determine commands indicated by the user inputs based on detecting location, intensity, duration, or other parameters of the touch inputs.

In embodiments, the application programming interface 508 and the client-facing application 510 may be implemented using various software environments, including but not limited to SAS and R package. SAS ("statistical analysis software") is a general purpose package (similar to Stata and SPSS) created by Jim Goodnight and N.C. State University colleagues. Ready-to-use procedures handle a wide range of statistical analyses, including but not limited to, analysis of variance, regression, categorical data analysis, multivariate analysis, survival analysis, psychometric analysis, cluster analysis, and nonparametric analysis. R package is free, general purpose package that complies with and runs on a variety of UNIX platforms.

Any combination of one or more computer readable medium(s) may be utilized to store the machine-learned models 512, the training application 514, and the training database 516. The one or more computer readable medium(s) may also be utilized to store the machine learning engine 518 and the variable selection machine learning models 520, the trained prediction models 522, the classification machine learning model 524. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described herein with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Although the figures show a specific order of method steps, the order of the steps may differ from what is depicted. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

In addition, unless otherwise indicated, numbers expressing quantities of ingredients, constituents, reaction conditions and so forth used in the specification and claims are to be understood as being modified by the term "about." Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±15% of the stated value; ±10% of the stated value; ±5% of the stated value; ±4% of the stated value; ±3% of the stated value; ±2% of the stated value; ±1% of the stated value; or ±any percentage between 1% and 20% of the stated value.

The following examples illustrate exemplary methods provided herein. These examples are not intended, nor are they to be construed, as limiting the scope of the disclosure. It will be clear that the methods can be practiced otherwise than as particularly described herein. Numerous modifications and variations are possible in view of the teachings herein and, therefore, are within the scope of the disclosure.

EXAMPLES

Example 1: Early Prediction of Vasospasm and Mortality Following Severe Traumatic Brain Injury (sTBI)

Post-traumatic vasospasm is one delayed cause of secondary brain ischemia and injury. Decisions regarding diagnosis and treatment of post-traumatic vasospasm, and prediction of mortality are currently based upon a combination of neurological examinations and imaging studies. Notably, serum inflammatory and neuronal markers detected early in the injury process have been shown to predict certain outcomes in patients with sTBI. Biomarkers, neurological examination, and radiographic findings are used for the prediction of vasospasm and mortality.

Methods. The data for model generation was obtained via Institutionally approved clinical study sTBI sTBI protocol. To date, 41 patients with sTBI have been enrolled. Thirty-six patients had sufficiently complete data that could be used for model generation. Backwards elimination was used to select model features with Random Forest (RF) models. Separate models were built for two target outcomes: vasospasm and death. Serum biomarker data was collected in the first 24-72 hours post-injury for 36 of 41 patients. Leave-one-out-cross validations was used with a sufficient number of iterations for convergence of sensitivity, specificity, and AUC. Results. For the 36 subjects used for modeling, 25 developed vasospasm (69%) and 8 died (22%). The model for vasospasm prediction produced a sensitivity of 0.85, specificity of 0.81, and AUC of 0.87. The RF vasospasm model included the features: Marshall Classification 2 (mild diffuse injury), presence of midline shift based on Rott CT, and temperature. The model for death produced a sensitivity of 0.86, specificity of 0.87, and AUC of 0.90. The RF death model included the features of serum eotaxin and transglutaminase-2.

Conclusion. Prediction results were obtained for the early detection of vasospasm and death in a sTBI population. These models prove useful for sTBI monitoring and treatment, and for triage in a resource-poor or combat setting.

Example 2: Estimating the Development of Heterotopic Ossification in Combat-Related Extremity Trauma The ectopic bone formation known as heterotopic ossification (HO) frequently develops after combat-related extremity trauma and was previously associated with high-energy trauma, hyper-inflammatory systemic response, wound bioburden and extremity amputations. In at least 60% of the cases, these patients may become symptomatic, requiring surgical excision. Once developed, HO represents a substantial barrier to patient recovery, functional mobility and return to duty. Risk stratification models indicating a higher chance of developing HO may help decide who should benefit most of early methods of prophylaxis such as the use of nonsteroidal anti-inflammatory drugs (NSAIDs). Therefore, whether the development of HO could be estimated by the cytokine response and clinical characteristics of patients with combat-related extremity trauma 24 hours after hospital admission was investigated.

Methods. The records of 73 patients with a total of 116 combat-related extremity wounds treated at the Walter Reed Hospital for the development of HO were examined. Patients were enrolled after hospital admission and samples of wound tissue, serum and wound effluent were collected immediately before the first surgical debridement and tested for a group of 32 cytokines associated with the inflammatory response. Wound surface was calculated by planimetry and critical colonization (CC, at least $10^5$ CFU/g of µl) was evaluated in samples of tissue and effluent. Variable selection based on wound surface, CC, and the level of cytokines was performed using the Boruta algorithm. Binary Random Forest models were trained with selected variables to estimate the likelihood of development of HO considering each independent wound. Model performance and 95% CI after cross-validation based on model training using default threshold of 0.5 was evaluated by the area under the receiver operating characteristic curve (AUC), sensitivity, and specificity.

Results. A total of 11 variables were selected for model training, including 10 serum cytokines and the wound surface area. A Random Forest model based on the level of IL-8, IL-2R, MIP-1α, GM-CSF, IL-15, IL-12, G-CSF, MIP-1β, IL-1RA, RANTES and the individual wound surface area had an AUC of 0.82 (0.78 to 0.87), sensitivity of 0.88 (0.85 to 0.91) and specificity of 0.61 (0.53 to 0.69). Conclusion. Systemic cytokine response in patients with extremity wounds may be used to estimate the development of HO in as early as 24 hours after of hospital admission, providing a highly efficient model. Results allow the development of an accurate clinical decision support tool for aiding on the treatment of these patients, as surgeons may have the option of considering use of prophylactic methods such as NSAIDS in patients with higher risk of development of HO.

Example 3: Advanced Modeling to Predict Bacteremia in Combat Trauma Patients Bacteremia is a life-threatening condition in the critically ill and injured.

Advanced Modeling to Predict Bacteremia in Combat Trauma Patients. Bacteremia is a life-threatening condition in the critically ill and injured. Tools to assist clinicians in predicting bacteremia could lead to a significant decrease in morbidity and mortality. Therefore, a model in combat trauma patients for identifying those at highest risk for bacteremia was developed.

Methods. The data for model generation was obtained from a prospective cohort consisting of 73 casualties with combat extremity wounds. The incidence of bacteremia was determined based on a review of inpatient records. Clinical expertise was used to select a candidate set of predictive features that included measurements of injury severity {Abbreviated Injury Scale (AIS) and Injury Severity Score (ISS)}, 32 serum biomarkers (chemokines, cytokines, and growth factors), and transfusion blood products (red blood cells, whole blood cells, platelets, fresh frozen plasma, and cryoprecipitate). The 44-potential predictive variables were reduced with a Random Forest (RF) algorithm and backwards elimination (BE) via complementary methods: (1) initiated with all 44 variables (2) only serum protein biomarkers after removing correlated ones (r>0.3). Following BE-mediated feature selection, both RF and logistic regression (LR) models were trained and tested with LOOCV (leave-one-out cross validation).

Results. The incidence of bacteremia was 22% (n=16). BE produced different variable sets when considering all variables, and a subset of variables using serum proteins alone. Via feature selection method 1, BE selected the variables ISS and serum biomarkers (MIG, IL-6, IL-7, IL-8). Method 2 resulted in the selection of the following serum biomarkers: GCSF, GMCSF, IL-1α, IL-1β, IL-2, IL-4, IL-6, IL-8, and VEGF. Using these variable sets, RFs were generated with AUCs of 0.82 and 0.84, sensitivities of 0.79 and 0.78, specificities of 0.74 and 0.78—all higher than the LR models.

Conclusion. Predictive modeling can allow for the prediction of the critical ill at risk for developing bacteremia using serum protein biomarker data alone or in conjunction with clinical variables.

Example 4: Predicting Severe Sepsis in Surgical ICU Patients

Sepsis is thought to affect 1.7 million American adults each year with 270,000 deaths.

Approximately 1 and 3 hospital deaths occur in patients with Sepsis. Severe Sepsis is defined as an extreme immunological response to infection leading to end organ damage, organ failure, and death. Sepsis is common among patients in the surgical ICU. Timely recognition of patients at risk for Sepsis in all forms is critical in successful application of therapeutic interventions. The goals for this study are: (1) development of model capable of a generalized prediction of Severe Sepsis; and (2) to predict Severe Sepsis in patients with traumatic wounds.

Methods. This study analyzed a dataset collected at a multicenter prospective study and composed of 567 patients (75.8% trauma and 24.2% non-trauma/surgical patients.) A total of 42 (7.41%) patients presented with severe sepsis at some point in their hospital stay. The median number of days till data collection was 2.4 days and 8.85 days till the diagnosis of severe sepsis. Based on the completeness of data, a subset of trauma and non-trauma/surgical patients with clinical and biomarker data available were used for analysis. Separate models were built for the combined cohort (N=112) and trauma cohort (N=96). Random forest modeling was conducted to predict the occurrence of severe sepsis. Feature selection was performed using backwards variable elimination. Models were trained and tested using leave-a-pair-out (one case and one control) cross validation. Data imbalance was addressed in training by up-sampling the smaller class.

Results. The incidence of severe sepsis was 14.3% (16/112) in the combined cohort and 12.5% (12/96) in the trauma cohort. The final combined cohort model resulted in a total of 8 features: (APACHE GCS verbal score, injury GCS verbal score, two penetrating abdominal trauma index variables, serum bFGF, serum IL-6, serum IL-8, and serum VEGF), with an area under the curve (AUC) of 0.83, sensitivity of 0.73, and specificity of and 0.89. For the trauma cohort model, 6 features were selected: (injury site variable, injury type variable, penetrating abdominal trauma index score, SOFA score, serum bFGF, and serum IL-6) with an AUC of 0.9, sensitivity and specificity of 0.88 and 0.77 respectively.

Conclusions. Random Forest models with predictive ability for the development of severe sepsis in surgical ICU patients.

Example 5: Clinical Risk Factors and Inflammatory Biomarkers of Post-Traumatic Acute Kidney Injury in Combat Patients Early identification of patients at risk of acute kidney injury (AKI) is important in the care of combat casualties and timely treatment may mitigate AKI. The aim of this study was to understand combat-related post-traumatic acute kidney injury (PTAKI) in recent military conflicts, identify clinical and biomarker associated variables, and train models to estimate PTAKI.

Methods. Data from a clinical cohort of 73 critically injured US military service members who sustained major combat related extremity wounds was used and serum and tissue biopsy samples were assayed for the expression of protein and mRNA biomarkers. Univariate and multivariate analyses were used to identify associated clinical and biomarker variables with AKI. An $\alpha<0.05$ was considered significant and trained models were evaluated with leave-one-out cross-validation by receiver-operator characteristic (ROC) and sensitivity/specificity at the threshold where their product was maximized. Features were selected for modeling using backwards elimination (BE).

Results. The incidence of PTAKI was 20.5%, 86% recovered baseline renal function and only two (15%) of the AKI group required RRT. PTAKI was associated with ISS, APACHE II, blood transfusion product, nosocomial infection, wound size, and serum levels of IL-2R, IL-6, and MCP1. Two models were trained: (1) BE with variables X (2) BE with variables Y. Model 1 resulted in the selection of with AIS head, vascular injury, ISS, and serum level of IL-3 with performance metrics: AUC of 0.91, sensitivity of 0.98, and specificity of 0.80. Model 2 (ISS, serum EGF, and tissue ACVR1, MMP10, and XCL1 expression) was able to estimate AKI with AUC of 0.93, sensitivities of 0.91, and specificities of 0.91.

Conclusion. The occurrence of AKI in combat casualties may be estimated based on injury characteristics and serum and tissue biomarkers. External validations of these models are necessary to generalize for all trauma patients.

Example 6: Predicting Acute Respiratory Distress Syndrome in Surgical ICU Patients Each year in the United States there are approximately 190,600 cases of acute respiratory distress syndrome (ARDS). These cases are associated with 74,500 deaths and 3.6 million hospital days. ARDS is characterized as a diffuse and acute lung injury stemming from a variety of etiologies. ARDS continues to be a possible complication in the treatment of trauma patients. Furthermore, effective treatment options remain limited. There is a need for the development of improved prevention strategies and methods to aid in early diagnosis and treatment. The aims of this study are: (1) development of model capable of a generalized prediction of ARDS and (2) to predict ARDS in patients with traumatic wounds.

Methods. Clinical and molecular biomarker data including serum ProCT levels collected from traumatically injured and surgical (non-trauma) patients presenting to three trauma centers were used. ARDS occurrence in this cohort was 8.82% (50/567). Median number of days post-injury was 2.4 for data collection, and median ARDS diagnosis was made 1 day post-injury. Based on the completeness of data, separate models were built for the combined cohort (N=168) and trauma cohort (N=105). Random forest modeling was conducted to predict the occurrence of severe sepsis. Feature selection was performed using an iterative backwards variable eliminations method. For the combined cohort, a model was trained and tested using leave-3-pairs-out (3 cases and 3 controls) for cross validation. For the trauma cohort models, leave-4-pairs-out cross-validation was employed. Data imbalance was addressed in training by up-sampling the smaller class.

Results. The incidence of ARDS was 9% (15/168) in the combined cohort and 12.4% (13/105) in the trauma cohort. A total of five final features (APACHE potassium score, injury GCS score verbal, injury site (head), total SOFA, and serum ProCT) were selected for the combined cohort model. The model gave an area under the curve (AUC) of 0.88, with sensitivity of 0.92 and specificity of 0.88. The trauma model resulted in 4 final features (APACHE potassium score, injury GCS verbal score, total SOFA, and serum ProCT) with an AUC of 0.9, sensitivity of 0.89, and specificity of 0.92.

Conclusion. These results illustrate development of a clinical decision support tool that classifies patients at risk of developing ARDS.

Example 7: A Comparison of Models to Predict Pneumonia in Combat Trauma Patients Pneumonia is a significant cause of morbidity and mortality in the critical ill and injured. The ability to predict patients at risk for pneumonia could lead to a reduction in morbidity and mortality. The purpose of this study was to compare two advanced modeling techniques to identify those at highest risk for developing pneumonia in a cohort of combat casualties.

Methods. The data for model generation was obtained from a prospective cohort consisting of 73 casualties with combat extremity wounds. Incidence of pneumonia was determined base review of inpatient records. Clinical expertise was used to select a candidate set of predictive features that included measurements of injury severity {Abbreviated Injury Scale (AIS) and Injury Severity Score (ISS)}, 32 serum biomarkers (chemokines, cytokines, and growth factors), and transfusion blood products (red blood cells, whole blood cells, platelets, fresh frozen plasma, and cryoprecipitate). The 44 potential predictive features were reduced with a Random Forest (RF) algorithm and backwards elimination (BE) via complementary methods: (1) initiated with all 44 variables (2) only serum markers after removing correlated variables (r>0.3). Following BE-mediated feature selection, both RF and logistic regression (LR) models were trained and tested with LOOCV (leave-one-out cross validation).

Results. The incidence of pneumonia was 12% (n=9). BE produced different variable sets when considering all variables, and just serum proteins alone. Using feature selection method 1, BE selected the variables ISS, AIS chest, and cryoprecipitate within the first 24 hours following injury for method 1 and FGF-basic, IL-2R, and IL-6 for method 2. Using these variable sets, RFs were generated with AUCs of 0.95 and 0.87—both higher than the LR models.

Conclusion. Advanced modeling allowed for the identification of clinical and biomarker data predictive of pneumonia in a cohort of combat trauma patients.

Example 8: Random Forest Model Predicts Acute Kidney Injury After Trauma Laparotomy Random Forest Model Predicts Acute Kidney Injury After Trauma Laparotomy. Despite advances in the management of critically ill patients, the incidence of acute kidney injury (AKI) remains high among trauma patients. Given the morbidity and mortality associated with AKI, the value of predictive modeling for identifying risk factors for the development of AKI was examined.

Methods. Clinical and molecular biomarker data were collected from patients undergoing exploratory laparotomy for abdominal trauma at a Level 1 trauma center between 2014 and 2017. Serum samples were collected within 24 hours after injury. AKI was defined as either (1) Increase in serum creatinine level of >0.3 mg/dL or >1.5 times baseline, (2) decrease in GFR by 50%, or (3) urine output <0.5 mL/kg per hour for >6 hours. Machine learning algorithms were employed to develop a model predicting AKI. Random forest (RF) was performed and features were selected using recursive variable elimination. The model was trained and tested with 145 records using leave-one-out cross validation.

Results. One hundred and forty-five patients were included (median age: 31, median ISS: 18). The incidence of AKI was 27.6% (40/145). AKI was diagnosed a median of 2 days (IQR: 0-13 days) post-injury. Overall mortality was 2% (1 AKI vs 2 non-AKI, p=1.0). Infectious complications were more common among AKI patients (10/40, 25%, versus 10/105, 9.5%; p=0.03). A total of 17/40 (42.5%) AKI patients progressed to Stage 3 AKI and 3/40 (7.5%) required renal replacement therapy. The final RF model resulted in three features (Sequential Organ Failure Assessment (SOFA) Score, Serum Monocyte Chemoattractant Protein-1 (MCP1), and serum Vascular endothelial growth factor (VEGF)) that predicted AKI with an area under the curve (AUC) of 0.739, a sensitivity of 0.817, and a specificity of 0.607. A logistic regression model with the RF final features predicted with an AUC of 0.722, a sensitivity of 0.769, and a specificity of 0.642.

Conclusion. Biomarkers may have diagnostic utility in the early identification of patients at risk of post-traumatic AKI Example 9: Early Prediction of Heterotopic Ossification Using Machine Learning Heterotopic ossification (HO) represents a significant complication of traumatic war injuries often effecting both recovery and physical functionality of wounded service members. HO is the formation of mature bone from osteoblastic progenitor cells within soft skeletal tissues, most often in the extremity, frequently associated with acute local trauma, spine/nervous system trauma, and surgery. HO begins forming within 48 hours of injury, however, there is a window of opportunity for preventive measures as clinical symptoms often take 1-3 months to develop. Nonsteroidal anti-inflammatory drugs have been shown to inhibit HO formation, if provided with temporal proximity to the point of trauma. HO significantly affects recovery as it can impede physical therapy as well as prosthetic fitting and use in extremity amputations. Radiographic imaging exams may show signs of HO formation approximately 4 weeks after injury. Significant factors, collected by approximately 5 days after injury, among trauma patients who developed HO versus those who did not were investigated to develop a predictive model for those who will form HO so they can be appropriately identified and treated prior to the development of clinical symptoms. For modeling approach, The Classification and Regression Tree (CART) algorithm due to its resultant model being a highly intuitive and interpretable decision tree which "resembles" a flow-chart representation of clinical practice guidelines was chosen.

Methods. Data collected from 73 military trauma patients with a majority of high-energy penetrating injuries from 2007 to 2012 after admission at the Walter Reed National Military Medical Center were evaluated. Three CART models were evaluated here: (1) Input variables included all potential predictive factors, collected at the initial surgical debridement, included patient demographics, injury characteristics, as well as serum and wound effluent biomarkers (2) Input variables were identified with Wilcoxon rank sum and Chi-square tests comparing HO and non-HO wounds (p<0.05) (3) a subset of the 35 significantly different variables identified by the approach used in Model 2 were further analyzed and a final group of 3 were selected based on the highest product of sensitivity and specificity. A total of 600 replicates were generated for the evaluation of sensitivity, specificity and AUC—represented by stable cumulative means (fluctuations smaller than 0.01). The 3 modeling approaches were used to generate 3 trees.

Results. The 73 patients had 116 wounds, which were used for predicting the occurrence of HO (45/116 or 39%). Model 3 (median AUC 0.83) performed best with a median sensitivity of 0.8 and median specificity of 0.9. Input variables to model 3 include: wound surface area, serum IL8, and effluent IL7. The most important variable was wound surface area. Model 1 (specificity 0.73, sensitivity 0.63) and model 2 (specificity 0.78, sensitivity 0.66) had lower performance.

Conclusion. There are currently no available models to accurately predict the development of HO in military trauma patients. Through data review of 73 military trauma patients, a model using 3 variables to predict HO with median sensitivity of 0.8, median specificity of 0.9 and median AUC of 0.79 was produced. The classification and Regression Tree model created indicates that the interaction between the biomarkers identified and wound surface area is predictive of HO formation.

Example 10: Utilizing Precision Medicine to Estimate Timing for Surgical Closure of Traumatic Extremity Wounds Extremity wounds are the most common occurring injuries sustained in military casualties, particularly during the recent conflicts [1] and are also frequent in civilians [2]. These extremity wounds may vary in severity from soft-tissue injuries to comminuted open fractures and traumatic amputations, and explosive blasts are the mechanism of injury in approximately 70% of military patients [3]. Considering the extensive amount of tissue damage, initial and ongoing microbiological contamination and further colonization by possible infective agents, regimented treatment of these wounds in military patients involves serial surgical debridements every 24 to 48 hours and negative pressure wound therapy, followed by eventual delayed wound closure (DWC) [4]. Wounds are closed by various techniques such as primary closure with approximation of borders by suture, coverage by skin grafts with or without dermal substitutes, local, or free myocutaneous or fasciocutaneous flaps [5-7].

The inflammatory response associated with these traumatic wounds is characterized by the production and secretion of several protein biomarkers [8, 9] such as interleukins, chemokines and growth factors both systemically into the blood stream and locally within the wound exudate. The level of these inflammatory mediators varies during the healing process and may be associated with the extent of injury and wound bioburden [10]. Additional conditions which may be associated with alterations of the concentration of inflammatory mediators include the development of heterotopic ossification [11] and wound failure (WF) [12], which is defined by the need of further surgical debridements after definitive wound closure or coverage is attempted. Successful healing is associated with an organized cytokine response, an effective treatment plan based on an adequate number of surgical debridements and efficient use of antibiotics before DWC. The time for DWC is primarily based on the gross appearance of healthy wound tissue, such as proper color, adequate consistency, muscle contractility in response to stimuli, and the capacity to bleed evaluated by examination of wound tissue [13-16]. However, this approach remains subjective and, in approximately 20% of the cases in military and civilian institutions, patients may require reoperation after DWC is attempted [17].

Machine-learning algorithms have been used successfully in multivariate analysis studies to assess the relationship of multiple associated variables to estimate the likelihood of patient survival, complications, and treatment outcomes in various fields of medicine [18-25]. In the present study, whether the timing of DWC may be estimated for each independent extremity wound was evaluated by analyzing possible variations in the level of local and systemic cytokines associated with the inflammatory response and wound healing. It was hypothesized that these variations in the level of cytokines could accurately predict the timing of successful wound closure in military and civilian patients with similar patterns of extremity trauma. To address this hypothesis, a machine learning approach based on a random forest algorithms was used. This multivariate analysis approach often allows an evaluation of relationships among variables and building of predictive models with high accuracy to estimate the likelihood of an outcome [26]. Using the random forests algorithm, cytokine concentrations and injury characteristics in wounds treated with multiple surgical debridements and DWC were evaluated to estimate the likelihood of WF, and the number of these debridements required before these wounds could be successfully closed.

Results. Patient Population Characteristics, Surgical Schedule and Wound Closure Outcome. A total of 73 combat casualties with 116 wounds and 81 civilian trauma patients with 114 wounds were evaluated. Civilians were of higher age, more gender-balanced, and their major injury mechanism was some form of motor vehicle accident, followed by gunshot. In the military, the major injury mechanism was the blast of improvised explosive devices and the majority their wounds were extremity amputations. In civilians, soft tissue injuries were the most prevalent type of wound. Patients had, on average, at least two surgical debridements after admission. Military had, on average, a higher ISS, if compared to civilians. Time of DWC, considered in number of days from injury, was higher in civilians, whose wounds were closed, on average by 17 days, if compared to military patients, in which DWC occurred on average, between 11 and 12 days. All military patients had surgical debridements with intervals of 1 to 3 days, starting from hospital admission to the day of wound closure. Of the 81 civilian patients, only 8 had a compatible surgical debridement schedule, with maximal surgical interval of 3 days until wound closure. Of the 73 military, 56 (90 wounds) had successful DWC. Among all civilians, 62 (22 wounds) also had successful wound closure without the need of further interventions. The remaining military and civilians had WF, requiring additional surgical debridements after DWC was attempted. The DWC outcome was further evaluated using Kaplan-Meier plots considering the day of closure as the event of for both military and civilians and separately for military and civilians. Patients with military wounds had the majority of wounds closed on earlier dates. In these patients, on average, approximately 50 to 60% of wounds which failed were closed in approximately 2 weeks from injury.

Cytokine Level Before Delayed Wound Closure. Patients were divided for cytokine analysis into 3 groups: military, civilians with similar surgical debridement schedule interval, and the remaining civilians with variable surgical debridement schedule interval, having occasional surgeries of more than 3 days apart. Serum and wound effluent level of cytokines were evaluated at the penultimate surgical debridement or visit event. This day was determined in order to allow an interval of approximately at least 2 days between sample collection and an eventual surgical wound closure attempt, in advance of model training. Civilians with variable surgical debridement schedules, either had a surgical debridement or a visit event including wound evaluation with sample collection preceding wound closure. In all cases, the penultimate event was considered for evaluating these patients. The level of all cytokines (32 in serum and 32 in wound effluent) was compared for these 3 groups. The largest number of significant isolated differences in the level of cytokines occurred between military patients and civilian with variable surgical debridement schedules. Significant variations in the level of cytokines were observed.

Selecting Variables for Model Training and Performance Evaluation. Considering militaries had, on average, wounds closed earlier with similar successful rates, variable selection for model training was performed in this cohort. Therefore, the Boruta algorithm was applied to select cytokines with a higher Z-score associated with the correct estimation of the wound closure outcome in military patients. Variables were analyzed based on the penultimate surgical debridement or visit event, as described. Of the 32 cytokines, 14 were considered relevant. These were ranked based on higher Z-scores starting from effluent IL-7, serum IL-7, effluent IL-6, serum VEGF, serum IFN-γ, effluent IL-4, serum EGF, serum RANTES, serum IP-10, effluent MIG, serum IL-10, serum IL-8, serum IL-6, and effluent IFN-γ. The level of these selected cytokines was further evaluated considering successful wound closure and WF and significant differences are shown for military patients, military and civilians with similar surgical schedule and for military and civilians with variable surgical schedule. Next, binary random forests models were training separately in these same three group combinations predict WF. Each model's performance variables included AUC, sensitivity and specificity. Sensitivity in models including civilians with variable surgical debridement schedule was markedly decreased (p<0.05), if compared to other models.

For the multi-class DWC model, wounds were classified as requiring one additional surgical debridement, two to five, or more than five. Similar to the WF model, the Boruta algorithm was applied again to military patients, although this time, potential cytokines were selected based only on the first surgical debridement considering the day of hospital admission based on days from injury. Cytokines with higher Z-scores were selected based on the number of surgical debridements necessary to successfully close each wound. A total of 10 cytokines were selected for model training. Inclusion of effluent IL-3 did not improve model performance, therefore this cytokine was excluded from the final model training and further evaluation. Cytokines used in the multi-class model training were further evaluated based on the required number of surgical debridements for successful DWC, as estimated in the model. Significant differences were detailed in FIG. 4B. The final multiclass random forests model trained based on the level of serum FGFb, serum IL-12, serum EGF, effluent G-CSF, effluent IL-7, serum IL-10, effluent TNFα, effluent VEGF, serum IL-1β, and serum VEGF demonstrated a mean AUC of 0.81 (95% CI, 0.79 to 0.83), mean sensitivity of 0.7 (95% CI, 0.65 to 0.76), and mean specificity of 0.4 (95% CI, 0.33 to 0.46) after 50 iterations of cross validation.

Discussion. Utilizing methods of precision medicine and machine learning, whether the timing of wound closure and healing outcome could be estimated by local and systemic cytokine response associated with traumatic extremity wounds was investigated. This estimation considered each wound independently, which could be one, two or, maximally, three per patient. In this novel approach, the present study focused variable selection for model training on the cytokine response. The goal was to use the possible variations in the level of inflammatory cytokines from the day of admission to the day of wound closure as an objective measurement of wound healing. Despite efforts to standardize treatment by military surgeons, the current treatment planning regarding timing of closure of these wounds remains subjective and dependent on the experience and opinions of each attending surgeon [4, 33]. Following each institution standard treatment guidelines, surgeons successfully achieved wound closure at the initial attempt in approximately 77% of the 116 wounds in military patients and approximately 80% of the 114 wounds in civilians evaluated in the present study, although military surgeons closed wounds earlier. However, the possibility of achieving successful wound closure at earlier dates in both groups of military and civilians could not be further evaluated because the timing of wound closure was decided by each attending surgeon. Therefore, it is possible that wounds treated with successful closure could be closed at even earlier dates.

In preparation for model training considering the penultimate event before closure, the local and systemic levels of cytokines were evaluated by univariate analysis, comparing military and civilian patient group combinations. This analysis showed an association of similar surgical debridement schedule interval with a more comparable cytokine response. Previous investigation showed the effects of surgical treatment interval are associated with variations on the cytokine response in extremity trauma [34]. In the present study, a variable surgical debridement schedule interval in civilian patients showed a distinct cytokine response in most functional groups of cytokines investigated. It was markedly represented by different level of classically described pro-inflammatory cytokines such as IL-1β, IL-6, and TNFα. Growth factors associated with wound healing such as EGF, FGFb and VEGF had significant different levels in civilian patients with a variable surgical schedule. In addition, among inflammatory mediators with chemotactic properties [35], Eotaxin (CCL11), IL-8 (CXCL8) and MIP-1β (CCL4) also had a distinct level in civilians with variable surgical schedule. Therefore, suggesting military and civilians with compatible surgical schedule had a more similar cytokine response.

Variable selection for model training may be performed by several methods such as backward elimination, in which less significant variables are eliminated and model performance is reanalyzed in their absence, forward selection, in which model performance is reviewed after a new variable is included, or the least absolute shrinkage and selection operator (LASSO) technique, which uses a regression-based analysis [36]. In the present study, Boruta algorithm, a method which allows relevant variables to be ranked, was used. This ranking is based on scores attributed to all original variables listed for selection compared to reference variables, known as shadow variables, which are created by random permutations of the original ones. This method has been extensively used and has shown to be highly effective in selecting variables for modeling using an approach based on random forest models [37]. A high score attributed to cytokines during variable selection, did not imply in a significant difference for the same cytokine according to each model estimated outcome. In binary models, which estimated the likelihood of successful DWC or WF, effluent IL-6 had the third highest score based on the Boruta algorithm, although this same cytokine had no significant differences if comparing any groups used for model training. In the multi-class model, which estimated the timing of successful wound closure, serum of both bFGF and EGF, which had the highest and third highest scores respectively had no significant differences comparing this model three groups of estimated categorical outcome. Therefore, considering the important numerous possible interactions and redundant functions of cytokines in vivo, these associations or the predictive value of cytokines, as biomarkers, should not be investigated only by univariate analysis alone.

In the present study, the aim is to train models using different events during treatment to work in screening and confirmatory roles. Therefore, after external validation, these models could be complementary in promoting decision support to clinical practice. This also aimed to minimize individual model limitations, such as the relatively small population size with no stratification according to mechanism and type of injury, or presence of bacterial infection, missing surgical events with no sample collection before patient study enrollment, different surgical duration time, and relatively different surgical technique used by each surgeon. The multiclass model trained using data close to hospital admission, would provide insight towards who would benefit from early wound closure or require more surgical interventions, and by consequence a possible longer hospitalization. In the sequence, the binary model could be applied and confirm an estimation of successful wound closure for each next surgery. Both models would provide information within a reasonable amount of time allowing the surgeon between one to two days to perform the next surgical intervention in each patient. The present binary models trained in military and in both military and civilians with a similar surgical schedule had similar AUC, sensitivity and specificity. Therefore, suggesting this model developed for military patients may be used by civilians with similar wounds, once both groups have a similar surgical schedule, which, in this case, is inferior to three days between surgeries. The multiclass model, given its high AUC and sensitivity, but low specificity, may be considered as a screening method. The binary model, which is highly specific, may function a confirmatory method. In addition to the performance of each model suggesting roles in screening and confirmation, both models aim to aid in associated clinical decisions, are based on a different stage of wound treatment, therefore complementary to each other.

It has been demonstrated, for the first time, that both the timing of DWC and the need of further surgical debridements may be estimated by cytokine response in the treatment of traumatic extremity wounds in both military and civilians with similar surgical schedule. This protocolized treatment approach has shown benefits in military patients such as earlier time of for traumatic extremity wound closure in patients frequently having a higher ISS, maintaining comparable low rates of WF, if compared to civilians. If followed by civilian centers, this treatment approach may show similar benefits in addition to also allow the possible utilization of clinical decision support tools based on statistical models developed in military trauma patients to aid in the treatment of similar trauma in civilians. These results may form the basis of novel clinical decision support tools and assist surgeons in determining the optimal time to close wounds while also aiding in estimating the necessary number of future surgeries. This would allow surgeons in as early as hours after patient admission to estimate the duration of the surgical treatment necessary to successfully close each extremity wound individually.

Conclusions. These results demonstrate that clinical decision support tools based on binary and multiclass models can be developed using compatible civilian and military populations with traumatic extremity wounds, as the cytokine response is highly influenced by surgical treatment. The use of these models in complementary roles may promote clinical support and minimize possible individual model limitations. These clinical decision support tools may help identify who may require serial debridements versus early closure, and precisely when traumatic extremity wounds should optimally be closed.

Example 11: Link Between Extracellular Mitochondrial DNA and Soluble CD40 Ligand in Post-Traumatic Sterile Inflammation Otherwise survivable combat injury can produce a massive systemic inflammatory response that ultimately results in organ failure and death. Traumatic tissue injury releases mitochondrial DNA (mtDNA) that stimulates Toll-like receptor 9 (TLR9). Platelets express functional TLR9, and activated platelets release soluble CD40 ligand (sCD40L) that produces a broad physiologic response through interaction with CD40. It was hypothesized that an increased extracellular mtDNA leads to sCD40L release from platelets producing systemic inflammation in trauma patients. Methods. Plasma was collected from 23 civilian trauma patients as part of the Surgical Critical Care Initiative. Patients were divided into two groups: those with injury severity score (ISS)≤10 who did not meet systemic inflammatory response syndrome (SIRS) criteria (n=9), and those with ISS>15 who met SIRS criteria (n=14). All plasma samples used were collected within 24 hours of injury. Plasma mtDNA concentration was measured by quantitative PCR, and plasma sCD40L concentration was measured by ELISA.

Results. In plasma from patients with ISS>15 who met SIRS criteria compared to patients with ISS≤10 who did not meet SIRS criteria, there was a higher concentration of both mtDNA (17.2±10.3 vs. 10.3±5.3, p=0.036) and sCD40L (96.8±48.9, vs. 65.3±16.2, p=0.046). There was significant correlation between plasma mtDNA concentration and sCD40L concentration ($R^2$ 0.1832, p=0.042).

Conclusions. There is a novel connection between release of extracellular mtDNA from damaged tissue, platelet activation through TLR9 stimulation, and platelet release of sCD40L resulting in the activation of downstream inflammatory pathways. Therapeutic disruption of this pathway could potentially decrease morbidity and mortality due to SIRS following survivable combat injury.

The embodiments and examples described above are provided by way of illustration only and should not be construed as limiting. Various modifications and changes may be made to the subject matter described herein without following the example embodiments and applications illustrated and described, and without departing from the true spirit and scope of the present disclosure, which is set forth in the following claims.

All publications, patents and patent applications cited in this specification are incorporated herein by reference in their entireties as if each individual publication, patent or patent application were specifically and individually indicated to be incorporated by reference.

The above description is for the purpose of teaching the person of ordinary skill in the art how to practice the subject of the present application, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

REFERENCES FOR EXAMPLE 10

1. Belmont P J, Jr., McCriskin B J, Sieg R N, Burks R, Schoenfeld A J. Combat wounds in Iraq and Afghanistan from 2005 to 2009. J Trauma Acute Care Surg. 2012; 73(1):3-12. Epub 2012 Jun. 30. doi: 10.1097/TA.0b013e318250bfb4. PubMed PMID: 22743366.
2. Banerjee M, Bouillon B, Shafizadeh S, Paffrath T, Lefering R, Wafaisade A, et al. Epidemiology of extremity injuries in multiple trauma patients. Injury. 2013; 44(8):1015-21. Epub 2013 Jan. 5. doi: 10.1016/j.injury.2012.12.007. PubMed PMID: 23287554.

3. Schoenfeld A J, Dunn J C, Bader J O, Belmont P J. The nature and extent of war injuries sustained by combat specialty personnel killed and wounded in Afghanistan and Iraq, 2003-2011. J Trauma Acute Care Surg. 2013; 75(2):287-91. doi: 10.1097/TA.0b013e31829a0970. PubMed PMID: 23887561.

4. Connolly M, Ibrahim Z R, Johnson O N. Changing paradigms in lower extremity reconstruction in war-related injuries. Mil Med Res. 2016; 3:9. Epub 2016 Mar. 31. doi: 10.1186/s40779-016-0080-7. PubMed PMID: 27042328; PubMed Central PMCID: PMCPMC4818384.

5. Sabino J, Polfer E, Tintle S, Jessie E, Fleming M, Martin B, et al. A decade of conflict: flap coverage options and outcomes in traumatic war-related extremity reconstruction. Plast Reconstr Surg. 2015; 135(3):895-902. doi: 10.1097/PRS.0000000000001025. PubMed PMID: 25415277.

6. Machen S. Management of traumatic war wounds using vacuum-assisted closure dressings in an austere environment. US Army Med Dep J. 2007:17-23. PubMed PMID: 20084702.

7. Geiger S, McCormick F, Chou R, Wandel A G. War wounds: lessons learned from Operation Iraqi Freedom. Plast Reconstr Surg. 2008; 122(1):146-53. doi: 10.1097/PRS.0b013e3181773d19. PubMed PMID: 18594399.

8. Chromy B A, Eldridge A, Forsberg J A, Brown T S, Kirkup B C, Jaing C, et al. Wound outcome in combat injuries is associated with a unique set of protein biomarkers. J Transl Med. 2013; 11:281. doi: 10.1186/1479-5876-11-281. PubMed PMID: 24192341; PubMed Central PMCID: PMCPMC3827499.

9. Hawksworth J S, Stojadinovic A, Gage F A, Tadaki D K, Perdue P W, Forsberg J, et al. Inflammatory biomarkers in combat wound healing. Annals of surgery. 2009; 250(6): 1002-7. PubMed PMID: 19953718.

10. Brown T S, Hawksworth J S, Sheppard F R, Tadaki D K, Elster E. Inflammatory response is associated with critical colonization in combat wounds. Surg Infect (Larchmt). 2011; 12(5):351-7. doi: 10.1089/sur.2010.110. PubMed PMID: 21936666.

11. Evans K N, Forsberg J A, Potter B K, Hawksworth J S, Brown T S, Andersen R, et al. Inflammatory cytokine and chemokine expression is associated with heterotopic ossification in high-energy penetrating war injuries. J Orthop Trauma. 2012; 26(11):e204-13. doi: 10.1097/BOT.0b013e31825d60a5. PubMed PMID: 22588530.

12. Forsberg J A, Elster E A, Andersen R C, Nylen E, Brown T S, Rose M W, et al. Correlation of procalcitonin and cytokine expression with dehiscence of wartime extremity wounds. J Bone Joint Surg Am. 2008; 90(3):580-8. doi: 10.2106/JBJS.G.00265. PubMed PMID: 18310708.

13. Tintle S M, Gwinn D E, Andersen R C, Kumar A R. Soft tissue coverage of combat wounds. J Surg Orthop Adv. 2010; 19(1):29-34. PubMed PMID: 20371004.

14. Tintle S M, Keeling J J, Shawen S B, Forsberg J A, Potter B K. Traumatic and trauma-related amputations: part I: general principles and lower-extremity amputations. J Bone Joint Surg Am. 2010; 92(17):2852-68. doi: 10.2106/JBJS.J.00257. PubMed PMID: 21123616.

15. Tintle S M, Baechler M F, Nanos G P, Forsberg J A, Potter B K. Traumatic and trauma-related amputations: Part II: Upper extremity and future directions. J Bone Joint Surg Am. 2010; 92(18):2934-45. doi: 10.2106/JBJS.J.00258. PubMed PMID: 21159994.

16. Forsberg J A, Potter B K, Polfer E M, Safford S D, Elster E A. Do inflammatory markers portend heterotopic ossification and wound failure in combat wounds? Clin Orthop Relat Res. 2014; 472(9):2845-54. doi: 10.1007/s11999-014-3694-7. PubMed PMID: 24879568; PubMed Central PMCID: PMCPMC4117913.

17. Tintle S M, Shawen S B, Forsberg J A, Gajewski D A, Keeling J J, Andersen R C, et al. Reoperation after combat-related major lower extremity amputations. J Orthop Trauma. 2014; 28(4):232-7. doi: 10.1097/BOT.0b013e3182a53130. PubMed PMID: 24658066.

18. Elster E A, Hawksworth J S, Cheng O, Leeser D B, Ring M, Tadaki D K, et al. Probabilistic (Bayesian) modeling of gene expression in transplant glomerulopathy. J Mol Diagn. 2010; 12(5):653-63. doi: 10.2353/jmoldx.2010.090101. PubMed PMID: 20688906; PubMed Central PMCID: PMCPMC2928430.

19. Forsberg J A, Eberhardt J, Boland P J, Wedin R, Healey J H. Estimating survival in patients with operable skeletal metastases: an application of a bayesian belief network. PLoS One. 2011; 6(5):e19956. doi: 10.1371/journal.pone.0019956. PubMed PMID: 21603644; PubMed Central PMCID: PMCPMC3094405.

20. Sohn S, Larson D W, Habermann E B, Naessens J M, Alabbad J Y, Liu H. Detection of clinically important colorectal surgical site infection using Bayesian network. J Surg Res. 2017; 209:168-73. Epub 2016 Dec. 30. doi: 10.1016/j.jss.2016.09.058. PubMed PMID: 28032554; PubMed Central PMCID: PMCPMC5391146.

21. Loghmanpour N A, Kanwar M K, Druzdzel M J, Benza R L, Murali S, Antaki J F. A new Bayesian network-based risk stratification model for prediction of short-term and long-term LVAD mortality. ASAIO J. 2015; 61(3):313-23. Epub 2015 Feb. 25. doi: 10.1097/MAT.0000000000000209. PubMed PMID: 25710772; PubMed Central PMCID: PMCPMC4414734.

22. Love A, Arnold C W, EI-Saden S, Liebeskind D S, Andrada L, Saver J, et al. Unifying acute stroke treatment guidelines for a Bayesian belief network. Stud Health Technol Inform. 2013; 192:1012. Epub 2013 Aug. 8. PubMed PMID: 23920786.

23. Ashby D. Bayesian statistics in medicine: a 25 year review. Stat Med. 2006; 25(21):3589-631. Epub 2006 Sep. 2. doi: 10.1002/sim.2672. PubMed PMID: 16947924.

24. Karhade A V, Ogink P, Thio Q, Broekman M, Cha T, Gormley W B, et al. Development of machine learning algorithms for prediction of discharge disposition after elective inpatient surgery for lumbar degenerative disc disorders. Neurosurg Focus. 2018; 45(5):E6. Epub 2018 Nov. 21. doi: 10.3171/2018.8.FOCUS18340. PubMed PMID: 30453463.

25. Bertsimas D, Dunn J, Velmahos G C, Kaafarani H M A. Surgical Risk Is Not Linear: Derivation and Validation of a Novel, User-friendly, and Machine-learning-based Predictive OpTimal Trees in Emergency Surgery Risk (POTTER) Calculator. Ann Surg. 2018; 268(4):574-83. Epub 2018 Aug. 21. doi: 10.1097/SLA.0000000000002956. PubMed PMID: 30124479.

26. Bountris P, Haritou M, Pouliakis A, Karakitsos P, Koutsouris D. A decision support system based on an ensemble of random forests for improving the management of women with abnormal findings at cervical cancer screening. Conf Proc IEEE Eng Med Biol Soc. 2015; 2015: 8151-6. Epub 2016 Jan. 7. doi: 10.1109/EMBC.2015.7320286. PubMed PMID: 26738186.

27. Lisboa F A, Bradley M J, Hueman M T, Schobel S A, Gaucher B J, Styrmisdottir E L, et al. Nonsteroidal anti-inflammatory drugs may affect cytokine response and benefit healing of combat-related extremity wounds. Surgery. 2017; 161(4):1164-73. Epub 2016 Dec. 3. doi: 10.1016/j.surg.2016.10.011. PubMed PMID: 27919449.

28. Morrison J J, Oh J, DuBose J J, O'Reilly D J, Russell R J, Blackbourne L H, et al. En-route care capability from point of injury impacts mortality after severe wartime injury. Ann Surg. 2013; 257(2):330-4. doi: 10.1097/SLA.0b013e31827eefcf. PubMed PMID: 23291661.

29. Kotwal R S, Howard J T, Orman J A, Tarpey B W, Bailey J A, Champion H R, et al. The Effect of a Golden Hour Policy on the Morbidity and Mortality of Combat Casualties. JAMA Surg. 2016; 151(1):15-24. doi: 10.1001/jamasurg.2015.3104. PubMed PMID: 26422778.

30. Forsberg J A, Potter B K, Wagner M B, Vickers A, Dente C J, Kirk A D, et al. Lessons of War: Turning Data Into Decisions. EBioMedicine. 2015; 2(9):1235-42. Epub 2015 Oct. 27. doi: 10.1016/j.ebiom.2015.07.022. PubMed PMID: 26501123; PubMed Central PMCID: PMCPMC4588374.

31. Benjamini Y, Yekutieli D. The Control of the False Discovery Rate in Multiple Testing under Dependency. The Annals of Statistics. 2001; 29(4):1165-88.

32. Hochberg Y, Benjamini Y. More powerful procedures for multiple significance testing. Stat Med. 1990; 9(7):811-8. Epub 1990 Jul. 1. PubMed PMID: 2218183.

33. Andersen R C, Fleming M, Forsberg J A, Gordon W T, Nanos G P, Charlton M T, et al. Dismounted Complex Blast Injury. J Surg Orthop Adv. 2012; 21(1):2-7. PubMed PMID: 22381504.

34. Pape H C, van Griensven M, Rice J, Gansslen A, Hildebrand F, Zech S, et al. Major secondary surgery in blunt trauma patients and perioperative cytokine liberation: determination of the clinical relevance of biochemical markers. J Trauma. 2001; 50(6):989-1000. Epub 2001 Jun. 27. PubMed PMID: 11426112.

35. Comerford I, McColl S R. Mini-review series: focus on chemokines. Immunol Cell Biol. 2011; 89(2):183-4. Epub 2011 Feb. 18. doi: 10.1038/icb.2010.164. PubMed PMID: 21326315.

36. Heinze G, Wallisch C, Dunkler D. Variable selection—A review and recommendations for the practicing statistician. Biom J. 2018; 60(3):431-49. Epub 2018 Jan. 3. doi: 10.1002/bimj.201700067. PubMed PMID: 29292533; PubMed Central PMCID: PMCPMC5969114.

37. Degenhardt F, Seifert S, Szymczak S. Evaluation of variable selection methods for random forests and omics data sets. Brief Bioinform. 2017. Epub 2017 Oct. 19. doi: 10.1093/bib/bbx124. PubMed PMID: 29045534.

What is claimed is:

1. A method of generating a model predicting one or more clinical outcomes for a subject, comprising:

generating, by a processor, a training database storing first values of a plurality of clinical parameters and clinical outcomes associated with a plurality of first subjects;

executing, by the processor, a plurality of variable selection machine learning models to select sets of model parameters from the plurality of clinical parameters for each variable selection machine learning model, wherein each set of the model parameters from the plurality of the model parameters comprises a different subset of the clinical parameters;

associating, by the processor, a plurality of classification machine learning models with the sets of model parameters, wherein each classification machine learning model of the plurality of classification machine learning model is associated with a set of model parameters of the sets of model parameters;

executing, by the processor, each one of the plurality of classification machine learning models and the associated set of model parameters to generate predictions of one or more clinical outcomes;

calculating, by the processor, a performance metric comparing a clinical outcome prediction of each combination of one of the plurality of classification machine learning models and a selected set of model parameters to one or more clinical outcomes, wherein the performance metric comprises a difference in Kappa score, a difference in sensitivity, and a difference in specificity;

selecting, by the processor, a respective combination of a candidate classification machine learning model and set of model parameters having a highest Kappa score, a highest sensitivity, and a specificity over a threshold; and outputting, by the processor, a plurality of models for predicting one or more clinical outcomes, each model comprising a selected combination of candidate classification machine learning model and set of model parameters.

2. The method of claim 1, further comprising pre-processing data that is stored in the training database including:

determining that a first value of at least one of the plurality of clinical parameters is missing;

estimating a reference value for the at least one of the plurality of clinical parameters that is missing; and storing the reference value as the first value of the at least one of the plurality of clinical parameters in the training database.

3. The method of claim 1, wherein the plurality of variable selection machine learning models comprise at least one of unsupervised machine learning algorithm, supervised machine learning algorithm, Backward Elimination algorithm, Grow-Shrink algorithm, Incremental Association Markov Blanket algorithm, Least Absolute Shrinkage and Selection Operator, Ridge Regression, Elastic Net, or Semi-Interleaved Hiton-PC algorithm.

4. The method of claim 1, wherein the classification machine learning model comprises at least one of linear discriminant analysis, classification and regression tree, decision tree learning, random forest model, nearest neighbor, support vector machine, logistic regression, generated linear model, Bayesian model, or neural network.

5. The method of claim 1, wherein selecting a candidate classification machine learning model in accordance with the performance metric further comprises:

executing decision curve analysis (DCA) with each classification machine learning model, the DCA indicating a net benefit of providing a treatment based on one or more clinical outcomes generated by the classification machine learning model; and selecting the classification machine learning model having a largest net benefit of providing the treatment as the candidate classification machine learning model.

6. The method of claim 1, further comprising:

cross-validating performances of the plurality of classification machine learning models.

7. The method of claim 6, wherein cross-validating performances comprises one or more of leave one out cross-validation, k fold, stratified cross-fold validation, or time-series cross-validation.

8. The method of claim 1, wherein the performance metric further comprises a sensitivity associated with the classification machine learning model and the associated set of model parameters and a specificity associated with the classification machine learning model and the associated set of model parameters.

9. The method of claim 1, wherein the plurality of clinical parameters comprise one or more biomarker clinical parameters, one or more data of the subject, one or more administration of blood transfusion products clinical parameters, surface wound injury, abdominal injury, one or more injury severity score clinical parameters, or a combination thereof.

10. The method of claim 9, wherein the biomarker clinical parameter comprises one or more level of interleukin-1α (IL-1α) in a sample from the subject, level of interleukin-Iβ (IL-Iβ) in a sample from the subject, level of interleukin-1 receptor agonist (IL-1RA) in a sample from the subject, level of interleukin-2 (IL-2) in a sample from the subject, level of interleukin-2 receptor (IL-2R) in a sample from the subject, level of interleukin-3 (IL-3) in a sample from the subject, level of interleukin-4 (IL-4) in a sample from the subject, level of interleukin-5 (IL-5) in a sample from the subject, level of interleukin-6 (IL-6) in a sample from the subject, level of interleukin-7 (IL-7) in a sample from the subject, level of interleukin-8 (IL-8) in a sample from the subject, level of interleukin-10 (IL-10) in a sample from the subject, level of interleukin-12 (IL-12) in a sample from the subject, level of interleukin-13 (IL-13) in a sample from the subject, level of interleukin-15 (IL-15) in a sample from the subject, level of interleukin-17 (IL-17) in a sample from the subject, level of tumor necrosis factor alpha (TNF-α) in a sample from the subject, level of granulocyte colony stimulating factor (G-CSF) in a sample from the subject, level of granulocyte macrophage colony stimulating factor (GM-CSF) in a sample from the subject, level of interferon alpha (IFN-α) in a sample from the subject, level of interleukin-8 (IL-8) in a sample from the subject, level of interleukin-10 (IL-10) in a sample from the subject, level of interferon gamma (IFN-γ) in a sample from the subject, level of epithelial growth factor (EGF) in a sample from the subject, level of basic epithelial growth factor (bFGF) in a sample from the subject, level of hepatocyte growth factor (HGF) in a sample from the subject, level of vascular endothelial growth factor (VEGF) in a sample from a subject, the level of monocyte chemoattractant protein-1 (CCL2/MCP-1) in a sample from a subject, level of macrophage inflammatory protein-1 alpha (CCL3/MIP-Ia) in a sample from a subject, level of macrophage inflammatory protein-1 beta (CCL4/MIP-Iβ) in a sample from a subject, level of CCL5/RANTES in a sample from a subject, the level of CCL11/eotaxin in a sample from a subject, level of monokine induced by gamma interferon (CXCL9/MIG) in a sample from a subject, level of interferon gamma-induced protein-10 (CXCL10/I P10) in a sample from a subject, level of basic fibroblast growth factor (bFGF) in a sample from a subject, level of mitochondrial DNA (mtDNA) in a sample from a subject, level of soluble CD40 ligand (sCD40L) in a subject, or level of transglutaminase 2 in a sample from a subject;

data of the subject comprise one or more of gender, age, date of injury, location of injury, presence of abdominal injury, mechanism of injury, wound depth, wound surface area, number of wound debridements, associated injuries, type of wound closure, success of wound closure, length of hospital stay, length of intensive care unit (ICU) stay, number of days on a ventilator, disposition from hospital, development of nosocomial infections, sequential organ failure assessment (SOFA), injury GCS score, Marshall Classification 2 (mild diffuse injury), midline shift based on Roterdam computed tomography, temperature, arterial pH, potassium score, vascular injury score, pulse rate, or $FiO_2$;

the administration of blood transfusion products clinical parameter comprises one or more of an amount of whole blood cells administered to the subject, amount of red blood cells (RBCs) administered to the subject, amount of packed red blood cells (PRBCs) administered to the subject, amount of platelets administered to the subject, summation of all blood transfusion products administered to the subject, or a level of total packed RBCs; and the injury severity score clinical parameter comprises one or more of Injury Severity Score (ISS), Abbreviated injury scale (AIS) of abdomen, AIS of chest (thorax), AIS of extremity, AIS of face, AIS of head, or AIS of skin.

11. The method of claim 1, wherein the one or more clinical outcomes comprise acute kidney injury, acute respiratory distress, bacteremia, heterotopic ossification, pneumonia, post-traumatic sterile inflammation, sepsis, wound closure, or vasospasm and/or mortality following traumatic brain injury, or a combination thereof.

12. A method for predicting one or more clinical outcomes for a subject comprising:

receiving, by a processor and from a second subject, a second value of at least one clinical parameter of a plurality of clinical parameters;

executing, by the processor, a pre-trained model for predicting one or more clinical outcomes of the second subject using the second value of at least one clinical parameter, wherein the model is pre-trained by performing operations comprising:

generating a training database storing first values of the plurality of clinical parameters and one or more clinical outcomes associated with a plurality of first subjects;

executing a plurality of variable selection machine learning models to select sets of model parameters from the plurality of clinical parameters for each variable selection machine learning model, wherein each set of the model parameters from the sets of model parameters comprises a different subset of the clinical parameters;

associating, by the processor, a plurality of classification machine learning models with the sets of model parameters, wherein each classification machine learning model of the plurality of classification machine learning model is associated with a set of model parameters of the sets of model parameters;

executing each one of the plurality of classification machine learning models the associated set of model parameters to generate predictions of the one or more clinical outcomes;

calculating a performance metric comparing a clinical outcome prediction of each combination of one of the plurality of classification machine learning models and a selected set of model parameters to one or more clinical outcomes, wherein the performance metric comprises a difference in Kappa score, a difference in sensitivity, and a difference in specificity;

selecting a respective combination of a candidate classification machine learning model and set of model parameters having a highest Kappa score, a highest sensitivity, and a specificity over a threshold;

outputting a plurality of models for predicting the one or more clinical outcomes, each model comprising a selected combination of candidate classification machine learning model and set of model parameters; and outputting, based on executing the second value with the pre-trained model, a predicted one or more clinical outcomes of the second subject.

13. The method of claim 12, wherein the operations to pre-train the model further comprise pre-processing data that is stored in the training database including:

determining that a first value of at least one of the plurality of clinical parameters is missing;

estimating a reference value for the at least one of the plurality of clinical parameters that is missing; and storing the reference value as the first value of the at least one of the plurality of clinical parameters in the training database.

14. The method of claim 12, wherein the plurality of variable selection machine learning models comprise at least one of unsupervised machine learning algorithm, supervised machine learning algorithm, Backward Elimination algorithm, Grow-Shrink algorithm, Incremental Association Markov Blanket algorithm, Least Absolute Shrinkage and Selection Operator, Ridge Regression, Elastic Net, or Semi-Interleaved Hiton-PC algorithm.

15. The method of claim 12, wherein the classification machine learning models comprises at least one of linear discriminant analysis, classification and regression tree, decision tree learning, random forest model, nearest neighbor, support vector machine, logistic regression, generated linear model, Bayesian model, or neural network.

16. The method of claim 12, wherein selecting the candidate classification machine learning model in accordance with the performance metric further comprises:

executing decision curve analysis (DCA) with each classification machine learning model, the DCA indicating a net benefit of providing a treatment based on one or more clinical outcomes generated by the classification machine learning model; and selecting the classification machine learning model having a largest net benefit of providing the treatment.

17. The method of claim 12, further comprising:

cross-validating performances of the plurality of classification machine learning models.

18. The method of claim 16, wherein cross-validating performances comprises one or more of leave one out cross-validation, k fold, stratified cross-fold validation, and time-series cross-validation.

19. The method of claim 12, wherein the performance metric further comprises a sensitivity associated with the classification machine learning model and the associated set of model parameters and a specificity associated with the classification machine learning model and the associated set of model parameters.

20. The method of claim 12, wherein the plurality of clinical parameters comprises one or more biomarker clinical parameters, one or more administration of blood transfusion products clinical parameters, surface wound injury, abdominal wound injury, one or more injury severity score clinical parameters, or a combination thereof.

21. The method of claim 20, wherein the biomarker clinical parameter comprises one or more level of interleukin-1α (IL-1α) in a sample from the subject, level of interleukin-Iβ (IL-Iβ) in a sample from the subject, level of interleukin-1 receptor agonist (IL-1RA) in a sample from the subject, level of interleukin-2 (IL-2) in a sample from the subject, level of interleukin-2 receptor (IL-2R) in a sample from the subject, level of interleukin-3 (IL-3) in a sample from the subject, level of interleukin-4 (IL-4) in a sample from the subject, level of interleukin-5 (IL-5) in a sample from the subject, level of interleukin-6 (IL-6) in a sample from the subject, level of interleukin-7 (IL-7) in a sample from the subject, level of interleukin-8 (IL-8) in a sample from the subject, level of interleukin-10 (IL-10) in a sample from the subject, level of interleukin-12 (IL-12) in a sample from the subject, level of interleukin-13 (IL-13) in a sample from the subject, level of interleukin-15 (IL-15) in a sample from the subject, level of interleukin-17 (IL-17) in a sample from the subject, level of tumor necrosis factor alpha (TNF-α) in a sample from the subject, level of granulocyte colony stimulating factor (G-CSF) in a sample from the subject, level of granulocyte macrophage colony stimulating factor (GM-CSF) in a sample from the subject, level of interferon alpha (IFN-α) in a sample from the subject, level of interleukin-8 (IL-8) in a sample from the subject, level of interleukin-10 (IL-10) in a sample from the subject, level of interferon gamma (IFN-γ) in a sample from the subject, level of epithelial growth factor (EGF) in a sample from the subject, level of basic epithelial growth factor (bFGF) in a sample from the subject, level of hepatocyte growth factor (HGF) in a sample from the subject, level of vascular endothelial growth factor (VEGF) in a sample from a subject, the level of monocyte chemoattractant protein-1 (CCL2/MCP-1) in a sample from a subject, level of macrophage inflammatory protein-1 alpha (CCL3/MIP-1α) in a sample from a subject, level of macrophage inflammatory protein-1 beta (CCL4/MIP-Iβ) in a sample from a subject, the level of CCL5/RANTES in a sample from a subject, the level of CCL11/eotaxin in a sample from a subject, level of monokine induced by gamma interferon (CXCL9/MIG) in a sample from a subject, level of interferon gamma-induced protein-10 (CXCL10/IP10) in a sample from a subject, level of basic fibroblast growth factor (bFGF) in a sample from a subject, level of mitochondrial DNA (mtDNA) in a sample from a subject, the level of soluble CD40 ligand (sCD40L) in a subject, or level of transglutaminase 2 in a sample from a subject;

data that comprises one or more of gender, age, date of injury, location of injury, presence of abdominal injury, mechanism of injury, wound depth, wound surface area, number of wound debridements, associated injuries, type of wound closure, success of wound closure, length of hospital stay, length of intensive care unit (ICU) stay, number of days on a ventilator, disposition from hospital, development of nosocomial infections, sequential organ failure assessment (SOFA), injury GCS score, Marshall Classification 2 (mild diffuse injury), midline shift based on Roterdam computed tomography, temperature, arterial pH, potassium score, vascular injury score, pulse rate, or $FiO_2$;

the administration of blood transfusion products clinical parameter comprises one or more of an amount of whole blood cells administered to the subject, amount of red blood cells (RBCs) administered to the subject, amount of packed red blood cells (PRBCs) administered to the subject, amount of platelets administered to the subject, summation of all blood transfusion products administered to the subject, or a level of total packed RBCs; and the injury severity score clinical parameter comprises one or more of Injury Severity Score (ISS), Abbreviated injury scale (AIS) of abdomen, AIS of chest (thorax), AIS of extremity, AIS of face, AIS of head, or AIS of skin.

22. The method of claim 12, wherein the one or more clinical outcomes comprise acute kidney injury, acute respiratory distress, bacteremia, heterotopic ossification, pneumonia, post-traumatic sterile inflammation, sepsis, wound closure, or vasospasm and/or mortality following traumatic brain injury, or a combination thereof.

\* \* \* \* \*